United States Patent [19]

Mattes et al.

[11] Patent Number: 5,786,140
[45] Date of Patent: Jul. 28, 1998

[54] DNA'S ENCODING SUCROSE ISOMERASE AND PALATINASE

[75] Inventors: Ralf Mattes; Kathrin Klein, both of Stuttgart; Hubert Schiweck; Markwart Kunz, both of Worms; Mohammad Munir, Kindenheim, all of Germany

[73] Assignee: Sudzucker Aktiengesellschaft Mannheim/Ochsenfurt, Germany

[21] Appl. No.: 374,155

[22] Filed: Jan. 18, 1995

[30] Foreign Application Priority Data

Jan. 19, 1994 [DE] Germany ............... 44 01 451.1
Apr. 22, 1994 [DE] Germany ............... 44 14 185.8

[51] Int. Cl.$^6$ ............ C12Q 1/68; C12N 15/63; C12N 1/21; C07H 21/04

[52] U.S. Cl. ............ 435/6; 435/320.1; 435/252.3; 536/23.2

[58] Field of Search ............ 536/23.2; 435/320.1, 435/252.3, 6

[56] References Cited

U.S. PATENT DOCUMENTS

| | | | |
|---|---|---|---|
| 4,359,531 | 11/1982 | Bucke et al. | 435/97 |
| 4,390,627 | 6/1983 | Lantero, Jr. | 435/180 |
| 4,670,387 | 6/1987 | Bucke et al. | 435/97 |
| 4,788,145 | 11/1988 | Munir | 435/100 |
| 4,857,461 | 8/1989 | Egerer et al. | 435/94 |
| 5,229,276 | 7/1993 | Sugitani et al. | 435/97 |
| 5,336,617 | 8/1994 | Sugitani et al. | 435/252.1 |

OTHER PUBLICATIONS

Nagai, Y. et al. (1994) "Characterization of alpha–glucosyl-transferase from Pseudomonas mesoacidophila MX–45" Biosci. Biotech. Biochem. 58(10):1789–1793, Oct. 1994.

Cheetham, P.S.J. (1984) "The extraction and mechanism of a novel isomaltulose-synthesizing enzyme from Erwini rhapontici" Biochem. J. 220:213–220, May 1984.

Iori, R., et al., "Oligonucleotide production by dextransucrase of Streptococcus bovis No. 148 isolated from bovine rumen", Biological Abstracts, Dec., 1990.

Itoh, Y., et al., "Synthesis of leucrose by dextranscurase and some conditions for the reaction", Biological Abstracts, Dec., 1990.

Iizuka, M., et al., "Susceptibility of leucrose to carbohydrates", Biological Abstracts, Jun., 1991.

Bugaenko, I.F., "Sweetening substances on the basis of sucrose", Chemical Abstracts, 1993–1994.

Crabb, W.D., et al., "Tools and Strategies for Cloning Studies," in Streips and Yasbin Modern Microbial Genetics, pp. 365–388, 1991.

Brock, T.D., et al., "Kinds of Plasmids and Their Biological Significance," Biology of Micro–Organisms, Chapter 8, Section 7.6–7.9, pp. 278–314, 1988.

Ernst–L. Winnacker, "From Genes to Clones: Introduction to Gene Technology," Weinheim (Federal Republic of Germany): VCH Verlagsgesellschaft (1987), pp. 383–395.

Primary Examiner—Eric Grimes
Assistant Examiner—Kawai Lau
Attorney, Agent, or Firm—Finnegan, Henderson, Farabow, Garrett & Dunner, L.L.P.

[57] ABSTRACT

The invention relates to sucrose isomerases, to DNA sequences coding therefor, and to novel processes for the production of non-cariogenic sugars.

29 Claims, 4 Drawing Sheets

FIG. 1

DNA'S ENCODING SUCROSE ISOMERASE AND PALATINASE

DESCRIPTION

The present invention relates to an improved process for the preparation of non-cariogenic sugars, in particular trehalulose and/or palatinose, using recombinant DNA technology.

The acariogenic sugar substitutes palatinose (isomaltulose) and trehalulose are produced on a large scale from sucrose by an enzymatic rearrangement using immobilized bacterial cells (for example of the species Protaminobacter rubrum, Erwinia rhapontici, Serratia plymuthica). This entails the α1→β2 glycosidic linkage existing between the two monosaccharide units of the disaccharide sucrose being isomerized to an α1→6 linkage in palatinose and to an α1→α1 linkage in trehalulose. This rearrangement of sucrose to give the two acariogenic disaccharides takes place with catalysis by the bacterial enzyme sucrose isomerase, also called sucrose mutase. Depending on the organism used, this reaction results in a product mixture which, besides the desired acariogenic disaccharides palatinose and trehalulose, also contains certain proportions of unwanted monosaccharides (glucose and/or fructose). These monosaccharide contents are a considerable industrial problem because elaborate purification procedures (usually fractional crystallizations) are necessary to remove them.

One object on which the present invention is based was thus to suppress as far as possible the formation of monosaccharides in the isomerization of sucrose to trehalulose and/or palatinose. Another object on which the present invention is based was to provide organisms which produce palatinose and/or trehalulose in a higher yield than do known organisms.

To achieve these objects, recombinant DNA molecules, organisms transformed with recombinant DNA molecules, recombinant proteins and an improved process for the preparation of non-cariogenic sugars, in particular of palatinose and/or trehalulose, are provided.

The invention relates to a DNA sequence which codes for a protein with a sucrose isomerase activity and comprises (a) one of the nucleotide sequences shown in SEQ ID NO. 1, SEQ ID NO. 2, SEQ ID NO. 3, SEQ ID NO. 9, SEQ ID NO. 11 or SEQ ID NO. 13, where appropriate without the signal peptide-coding region, (b) a nucleotide sequence corresponding to the sequences from (a) within the scope of the degeneracy of the genetic code, or (c) a nucleotide sequence which hybridizes with the sequences from (a) and/or (b).

In the context of the present invention, the term "protein with a sucrose isomerase activity" is intended to embrace those proteins which are able to isomerize sucrose to other disaccharides with conversion of the α1→β2 glycosidic linkage between glucose and fructose in sucrose into another glycosidic linkage between two monosaccharide units, in particular into an α1→6 linkage and/or an α1→α1 linkage. The term "protein with a sucrose isomerase activity" therefore particularly preferably relates to a protein which is able to isomerize sucrose to palatinose and/or trehalulose. Moreover, the proportion of palatinose and trehalulose in the total disaccharides formed by isomerization of sucrose is preferably ≧2%, particularly preferably ≧20% and most preferably ≧50%.

The nucleotide sequence shown in SEQ ID NO. 1 codes for the complete sucrose isomerase from the microorganism Protaminobacter rubrum (CBS 547.77) including the signal peptide region. The nucleotide sequence shown in SEQ ID NO. 2 codes for the N-terminal section of the sucrose isomerase from the microorganism Erwinia rhapontici (NCPPB 1578) including the signal peptide region. The nucleotide sequence shown in SEQ ID NO. 3 codes for a section of the sucrose isomerase from the microorganism SZ 62 (Enterobacter spec.).

The region which codes for the signal peptide in SEQ ID NO. 1 extends from nucleotide 1–99. The region coding for the signal peptide in SEQ ID NO. 2 extends from nucleotide 1–108. The DNA sequence according to the present invention also embraces the nucleotide sequences shown in SEQ ID NO. 1 and SEQ ID NO. 2 without the region coding for the signal peptide because the signal peptide is, as a rule, necessary only for correct localization of the mature protein in a particular cell compartment (for example in the periplasmic space between the outer and inner membrane, in the outer membrane or in the inner membrane) or for extracellular export, but not for the enzymatic activity as such. The present invention thus furthermore embraces sequences which also code for the mature protein (without signal peptide) and are operatively linked to heterologous signal sequences, in particular to prokaryotic signal sequences as described, for example, in E. L. Winnacker, Gene und Klone, Eine Einführung in die Gentechnologie, VCH-Verlagsgesellschaft Weinheim, Germany (1985), p. 256.

Nucleotide sequence SEQ ID NO. 9 codes for a variant of the isomerase from Protaminobacter rubrum. Nucleotide sequence SEQ ID NO. 11 codes for the complete isomerase from the isolate SZ 62. Nucleotide sequence SEQ ID NO. 13 codes for most of the isomerase from the microorganism MX-45 (FERM 11808 or FERM BP 3619).

Besides the nucleotide sequences shown in SEQ ID NO. 1, SEQ ID NO. 2, SEQ ID NO. 3, SEQ ID NO. 9, SEQ ID NO. 11 or SEQ ID NO. 13, and nucleotide sequences corresponding to one of these sequences within the scope of the degeneracy of the genetic code, the present invention also embraces a DNA sequence which hybridizes with one of these sequences, provided that it codes for a protein which is able to isomerize sucrose. The term "hybridization" according to the present invention is used as in Sambrook et al. (Molecular Cloning, A Laboratory Manual, Cold Spring Harbor Laboratory Press (1989), 1.101–1.104). According to the present invention, hybridization is the word used when a positive hybridization signal is still observed after washing for 1 hour with 1×SSC and 0.1% SDS at 55° C., preferably at 62° C. and particularly preferably at 68° C., in particular for 1 hour in 0.2×SSC and 0.1% SDS at 55° C., preferably at 62° C. and particularly preferably at 68° C. A nucleotide sequence which hybridizes under such washing conditions with one of the nucleotide sequences shown in SEQ ID NO:1 or SEQ ID NO:2, or with a nucleotide sequence which corresponds thereto within the scope of the degeneracy of the genetic code, is a nucleotide sequence according to the invention.

The DNA sequence according to the invention preferably has (a) one of the nucleotide sequences shown in SEQ ID NO. 1, SEQ ID NO. 2, SEQ ID NO. 3, SEQ ID NO. 9, SEQ ID NO. 11 or SEQ ID NO. 13, where appropriate without the signal peptide-coding region, or (b) a nucleotide sequence which is at least 70% homologous with the sequences from (a).

The DNA sequence according to the invention preferably also has an at least 80% homologous nucleotide sequence to the conserved part-regions of the nucleotide sequences shown in SEQ ID NO. 1, SEQ ID NO. 2, SEQ ID NO. 3, SEQ ID NO. 9, SEQ ID NO. 11 or SEQ ID NO. 13. These conserved part-regions are, in particular, from nucleotide 139–186, nucleotide 256–312, nucleotide 328–360, nucleotide 379–420 and/or nucleotide 424–444 in the nucleotide sequence shown in SEQ ID NO. 1.

In a particularly preferred embodiment, the DNA sequence according to the invention has an at least 80% homologous, in particular an at least 90% homologous, nucleotide sequence to the part-regions (a) nucleotide 139–155 and/or (b) nucleotide 625–644 of the nucleotide sequence shown in SEQ ID NO. 1.

Oligonucleotides derived from the above sequence regions have proved suitable as primers for PCR amplification of isomerase fragments from the genomic DNA of a large number of tested microorganisms, for example Protaminobacter rubrum (CBS 547, 77), Erwinia rhapontici (NCPPB 1578), isolate SZ 62 and Pseudomonas mesoacidophila MX-45 (FERM 11808).

Particularly preferably used for this purpose are the following oligonucleotides, where appropriate in the form of mixtures, where the bases in parentheses can be present as alternatives:

Oligonucleotide I (17 nt):

5'-TGGTGGAA(A,G)GA(G,A)GCTGT-3'(SEQ ID NO: 17)

Oligonucleotide II (20 nt):

5'-TCCCAGTTCAG(G,A)TCCGGCTG-3'(SEQ ID NO: 18)

Oligonucleotide I is derived from nucleotides 139–155 of SEQ ID NO. 1, and oligonucleotide II is derived from the sequence, complementary to nucleotides 625–644, of SEQ ID NO. 1. The differences between the homologous part-regions of the DNA sequences according to the invention and the sequences called oligonucleotide I and oligonucleotide II are preferably in each case not more than 2 nucleotides and particularly preferably in each case not more than 1 nucleotide.

In another particularly preferred embodiment of the present invention, the DNA sequence has an at least 80% homologous, in particular an at least 90% homologous, nucleotide sequence to the part-regions of (c) nucleotide 995–1013 and/or (d) nucleotide 1078–1094 of the nucleotide sequence shown in SEQ ID NO. 1.

Oligonucleotides derived from the above sequence regions hybridize with sucrose isomerase genes from the organisms Protaminobacter rubrum and Erwinia rhapontici. The following oligonucleotides, where appropriate in the form of mixtures, are particularly preferably used, where the bases indicated in parentheses may be present as alternatives:

Oligonucleotide III (19 nt):

AAAGATGGCG(G,T)CGAAAAGA (SEQ NO ID: 19)

oligonucleotide IV (17 nt):

5'-TGGAATGCCTT(T,C)TTCTT-3'(SEQ ID NO: 20)

Oligonucleotide III is derived from nucleotides 995–1013 of SEQ ID NO. 1, and oligonucleotide IV is derived from nucleotides 1078–1094 of SEQ ID NO. 1. The differences between the homologous part-regions of the DNA sequences according to the invention and the sequences called oligonucleotide III and IV are preferably in each case not more than 2 nucleotides and particularly preferably in each case not more than 1 nucleotide.

Nucleotide sequences according to the invention can be obtained in particular from microorganisms of the genera Protaminobacter, Erwinia, Serratia, Leuconostoc, Pseudomonas, Agrobacterium and Klebsiella. Specific examples of such microorganisms are Protoaminobacter rubrum (CBS 547,77), Erwinia rhapontici (NCPPB 1578), Serratia plymuthica (ATCC 15928), Serratia marcescens (NCIB 8285), Leuconostoc mesenteroides NRRL B-521f (ATCC 10830a), Pseudomonas mesoacidophila MX-45 (FERM 11808 or FERM BP 3619), Agrobacterium radiobacter MX-232 (FERM 12397 or FERM BP 3620), Klebsiella subspecies and Enterobacter species. The nucleotide sequences according to the invention can be isolated in a simple manner from the genome of the relevant microorganisms, for example using oligonucleotides from one or more of the conserved regions of SEQ ID NO. 1, SEQ ID NO. 2, SEQ ID NO. 3, SEQ ID NO. 9, SEQ ID NO. 11 and SEQ ID NO: 13, by standard techniques of amplification and/or hybridization, and be characterized. The nucleotide sequences according to the invention are preferably obtained by PCR amplification of the genomic DNA of the relevant organism using oligonucleotides I and II. A part-fragment of the relevant sucrose isomerase gene is obtained in this way and can subsequently be used as hybridization probe for isolating the complete gene from a gene bank of the relevant microorganism. Alternatively, the nucleotide sequences can be obtained by producing a gene bank from the particular organism and direct screening of this gene bank with oligonucleotides I, II, III and/or IV.

The present invention further relates to a vector which contains at least one copy of a DNA sequence according to the invention. This vector can be any prokaryotic or eukaryotic vector on which the DNA sequence according to the invention is preferably under the control of an expression signal (promoter, operator, enhancer, etc.). Examples of prokaryotic vectors are chromosomal vectors such as, for example, bacteriophages (for example bacteriophage λ) and extrachromosomal vectors such as, for example, plasmids, with circular plasmid vectors being particularly preferred. Suitable prokaryotic vectors are described, for example, in Sambrook et al., supra, Chapters 1–4.

A particularly preferred example of a vector according to the invention is the plasmid pHWS 88 which harbors a sucrose isomerase gene from Protaminobacter rubrum (with the sequence shown in SEQ ID NO. 1) under the control of the regulatable tac promoter. The plasmid pHWS 88 was deposited on Dec. 16, 1993, at the Deutsche Sammlung von Mikroorganismen und Zellkulturen (DSM), Mascheroder Weg 1b, 38124 Braunschweig, Germany, under the deposit number DSM 8824 in accordance with the provisions of the Budapest Treaty.

In another preferred embodiment of the present invention, the vector according to the invention is a plasmid which is present in the host cell with a copy number of less than 10, particularly preferably with a copy number of 1 to 2 copies per host cell. Examples of vectors of this type are, on the one hand, chromosomal vectors such as, for example, bacteriophage λ or F plasmids. F plasmids which contain the sucrose isomerase gene can be prepared, for example, by transformation of an E. coli strain which contains an F plasmid with a transposon containing the sucrose isomerase gene, and subsequent selection for recombinant cells in which the transposon has integrated into the F plasmid. One example of a recombinant transposon of this type is the plasmid pHWS 118 which contains the transposon Tn 1721 Tet and was prepared by cloning a DNA fragment containing the sucrose isomerase gene from the above-described plasmid pHWS 88 into the transposon pJOE 105 (DSM 8825).

On the other hand, the vector according to the invention can also be a eukaryotic vector, for example a yeast vector (for example YIp, YEp, etc.) or a vector suitable for higher cells (for example a plasmid vector, viral vector, plant vector). Vectors of these types are familiar to the person skilled in the area of molecular biology so that details thereof need not be given here. Reference is made in this connection in particular to Sambrook et al., supra, Chapter 16.

The present invention further relates to a cell which is transformed with a DNA sequence according to the invention or a vector according to the invention. In one embodiment, this cell is a prokaryotic cell, preferably a Gram-negative prokaryotic cell, particularly preferably an enterobacterial cell. It is moreover possible on the one hand to use a cell which contains no sucrose isomerase gene of its own, such as, for example, E. coli, but it is also possible, on the other hand, to use cells which already contain such a gene on their chromosome, for example the microorganisms mentioned above as source of sucrose isomerase genes. Preferred examples of suitable prokaryotic cells are *E. coli*, *Protaminobacter rubrum* or *Erwinia rhapontici* cells. The transformation of prokaryotic cells with exogenous nucleic acid sequences is familiar to a person skilled in the area of molecular biology (see, for example, Sambrook et al., supra, Chapter 1-4).

In another embodiment of the present invention, the cell according to the invention may, however, also be a eukaryotic cell such as, for example, a fungal cell (for example yeast), an animal or a plant cell. Methods for the transformation or transfection of eukaryotic cells with exogenous nucleic acid sequences are likewise familiar to the person skilled in the area of molecular biology and need not be explained here in detail (see, for example, Sambrook et al., Chapter 16).

The invention also relates to a protein with a sucrose isomerase activity as defined above, which is encoded by a DNA sequence according to the invention. This protein preferably comprises (a) one of the amino-acid sequences shown in SEQ ID NO. 4, SEQ ID NO. 5, SEQ ID NO. 6, SEQ ID NO. 10, SEQ ID NO. 12 or SEQ ID NO. 14, where appropriate without the signal peptide region or (b) an amino-acid sequence which is at least 80% homologous with the sequences from (a).

The amino-acid sequence shown in SEQ ID NO. 4 comprises the complete sucrose isomerase from *Protaminobacter rubrum*. The signal peptide extends from amino acid 1–33. The mature protein starts at amino acid 34. The amino-acid sequence shown in SEQ ID NO. 5 comprises the N-terminal section of the sucrose isomerase from *Erwinia rhapontici*. The signal peptide extends from amino acid 1–36. The mature protein starts at amino acid 37. The amino-acid sequence shown in SEQ ID NO. 6 comprises a section of the sucrose isomerase from the microorganism SZ 62. FIG. 1 compares the amino-acid sequences of the isomerases from *P. rubrum*, *E. rhapontici* and SZ 62.

Amino-acid sequence SEQ ID NO. 10 comprises a variant of the isomerase from P. rubrum. Amino-acid sequence SEQ ID NO. 12 comprises the complete isomerase from SZ 62. This enzyme has a high activity at 37° C. and produces only a very small proportion of monosaccharides. Amino-acid sequence SEQ ID NO. 14 comprises a large part of the isomerase from MX-45. This enzyme produces about 85% trehalulose and 13% palatinose.

The protein according to the invention particularly preferably has an at least 90% homologous amino-acid sequence to conserved part-regions from the amino-acid sequences shown in SEQ ID NO. 4, SEQ ID NO. 5, SEQ ID NO. 6, SEQ ID NO. 10, SEQ ID NO. 12 or SEQ ID NO. 14, especially in part-regions from (a) amino acid 51–149, (b) amino acid 168–181, (c) amino acid 199–250, (d) amino acid 351–387 and/or (e) amino acid 390–420 of the amino-acid sequence shown in SEQ ID NO. 4.

It is possible by means of the abovementioned DNA sequences, vectors, transformed cells and proteins to provide a sucrose isomerase activity in a simple manner without interfering additional enzymatic activities.

It is possible for this purpose on the one hand to obtain the sucrose isomerase by recombinant DNA technology as constituent of an extract from the host organism or in isolated and purified form (for example by expression in *E. coli*). This preferably purified and isolated sucrose isomerase enzyme can be used, for example, in immobilized form, for the industrial production of acariogenic sugars such as, for example, trehalulose and/or palatinose by reaction of sucrose in an enzyme reactor. The immobilization of enzymes is familiar to a skilled person and need not be described in detail here.

On the other hand, the production of acariogenic sugars from sucrose can also take place in a complete microorganism, preferably in immobilized form. Cloning of the abovementioned sucrose isomerase gene into an organism without or with reduced palatinose and/or trehalulose metabolism (that is to say in an organism which is unable significantly to degrade the above-mentioned sugars) allows generation of a novel organism which, owing to the introduction of exogenous DNA, is able to produce acariogenic disaccharides with negligible formation of monosaccharides. Thus, suitable for introducing the sucrose isomerase gene is, on the one hand, an organism which is unable to utilize palatinose and/or trehalulose (for example *E. coli*, bacillus, yeast) and, on the other hand, an organism which would in principle be able to utilize palatinose and/or trehalulose but has reduced palatinose and/or trehalulose metabolism owing to undirected or directed mutation.

The term "reduced palatinose and/or trehalulose metabolism" means for the purpose of the present invention that a whole cell of the relevant organism produces, on utilization of sucrose as C source, acariogenic disaccharides but is able to utilize the latter to only a small extent in metabolism, for example by degrading them to monosaccharides. The organism preferably produces less than 2.5%, particularly preferably less than 2%, most preferably less than 1%, of glucose plus fructose based on the total of acariogenic disaccharides and monosaccharide degradation products at a temperature of 15°–65° C., in particular of 25°–55° C.

The present invention thus further relates to a cell which contains at least one DNA sequence coding for a protein with a sucrose isomerase activity, and has a reduced palatinose and/or trehalulose metabolism as defined above. A cell of this type produces larger proportions of the non-cariogenic disaccharides trehalulose and/or palatinose and reduced amounts of the interfering byproducts glucose and fructose.

It is possible in one embodiment of the present invention to reduce the palatinose and/or trehalulose metabolism by partial or complete inhibition of the expression of invertase and/or palatinase genes which are responsible for the intracellular degradation of palatinose and/or trehalulose. This inhibition of gene expression can take place, for example, by site-directed mutagenesis and/or deletion of the relevant genes. A site-directed mutation of the palatinase gene shown in SEQ ID NO. 7 or of the palatinose hydrolase gene shown in SEQ ID NO. 15 can take place, for example, by introduction of a vector which is suitable for homologous chromosomal recombination and which harbors a mutated palatinase gene, and selection for organisms in which such a recombination has taken place. The principle of selection by genetic recombination is explained in E. L. Winnacker, Gene und Klone, Eine Einführung in die Gentechnologie (1985), VCH-Verlagsgesellschaft Weinheim, Germany, pp. 320 et seq.

It is furthermore possible to obtain organisms according to the invention with reduced palatinose and/or trehalulose metabolism by non-specific mutagenesis from suitable starting organisms and selection for palatinase-deficient mutants. One example of a palatinase-deficient mutant of this type is the *Protaminobacter rubrum* strain SZZ 13 which was deposited on Mar. 29, 1994, at the Deutsche Sammlung von Mikroorganismen und Zellkulturen (DSM), Mascheroder Weg 1b, 38124 Braunschweig, Germany, under deposit number DSM 9121 in accordance with the provisions of the Budapest Treaty. This microorganism was prepared by non-specific mutagenesis of *P. rubrum* wildtype cells with N-methyl-N'-nitro-N-nitrosoguanidine and is distinguished in that it is no longer able to cleave the non-cariogenic sugars trehalulose and palatinose to glucose and fructose. Selection for such mutants can take place, for example, by using MacConkey palatinose media or minimal salt media with palatinose or glucose as sole C source. The mutants which are white on MacConkey palatinose medium (MacConkey Agar Base from Difco Laboratories, Detroit, Mich., USA (40 g/l) and 20 g/l palatinose) or which grow on minimal salt media with glucose as sole C source but not on corresponding media with palatinose as sole C source are identified as palatinase-deficient mutants.

The present invention furthermore relates to a method for isolating nucleic acid sequences which code for a protein with a sucrose isomerase activity, wherein a gene bank from a donor organism which contains a DNA sequence coding for a protein with a sucrose isomerase activity is set up in a suitable host organism, the clones of the gene bank are examined, and the clones which contain a nucleic acid coding for a protein with sucrose isomerase activity are isolated. The nucleic acids which are isolated in this way and code for sucrose isomerase can in turn be used for introduction into cells as described above in order to provide novel producer organisms of acariogenic sugars.

In this method, the chosen host organism is preferably an organism which has no functional genes of its own for palatinose metabolism, in particular no functional palatinase and/or invertase genes. A preferred host organism is *E. coli*. To facilitate characterization of palatinose-producing clones it is possible on examination of the clones in the gene bank for sucrose-cleaving clones and the DNA sequences which are contained therein and originate from the donor organism to be isolated and transformed in an *E. coli* strain which does not utilize galactose and which is used as screening strain for the clones in the gene bank.

On the other hand, the examination of the clones in the gene bank for DNA sequences which code for a protein with a sucrose isomerase activity can also take place using nucleic acid probes derived from the sequences SEQ ID NO. 1, SEQ ID NO. 2, SEQ ID NO. 3, SEQ ID NO. 9, SEQ ID NO. 11 and SEQ ID NO. 13 which code for the sucrose isomerase genes from *Protaminobacter rubrum, Erwinia rhapontici* and the isolate SZ 62. A DNA fragment obtained by PCR reaction with oligonucleotides I and II as primers, or the oligonucleotides III and/or IV, are particularly preferably used as probes.

The present invention further relates to a process for the production of non-cariogenic sugars, in particular trehalulose and/or palatinose, which comprises using for the production of the sugars (a) a protein with sucrose isomerase activity in isolated form, (b) an organism which is transformed with a DNA sequence which codes for protein with sucrose isomerase activity, or with a vector which contains at least one copy of this DNA sequence, (c) an organism which contains at least one DNA sequence coding for a protein with a sucrose isomerase activity, and has a reduced palatinose and/or trehalulose metabolism, and/or (d) an extract from such a cell or from such an organism.

The process is generally carried out by contacting the protein, the organism or the extract in a suitable medium with sucrose under conditions such that the sucrose is at least partly converted by the sucrose isomerase into acariogenic disaccharides. Subsequently, the acariogenic disaccharides are obtained from the medium or the organism and purified in a known manner.

In a preferred embodiment of this process, the organism, the protein or the extract is used in immobilized form. Proteins (in pure form or in extracts) are preferably immobilized by coupling of reactive side groups (for example $NH_2$ groups) to a suitable carrier. Immobilization of cells takes place, for example, in a sodium alginate/calcium chloride solution. A review of suitable methods for immobilizing cells and proteins is given, for example, in *I. Chibata* (Immobilized Enzymes, John Wiley and Sons, New York, London, 1978).

It is possible on use of a cell transformed with the sucrose isomerase gene to increase the rate of production of acariogenic sugars by comparison with known organisms by increasing the number of gene copies in the cell and/or by increasing the expression rate in a combination with strong promoters. It is furthermore possible by transformation of a cell which is unable or able to only a limited extent to utilize acariogenic sugars with the sucrose isomerase gene to produce a transformed cell with whose aid it is possible to obtain acariogenic sugars, in particular palatinose and/or trehalulose, without or with fewer byproducts.

On use of a microorganism with reduced palatinose and/or trehalulose metabolism, which already contains a functional sucrose isomerase gene, transformation with an exogenous sucrose isomerase gene is not essential but may be carried out to improve the yields.

Finally, the present invention also relates to a DNA sequence which codes for a protein with palatinase or palatinose hydrolase activity and comprises (a) one of the nucleotide sequences shown in SEQ ID NO. 7 or SEQ ID NO. 15, (b) a nucleotide sequence which corresponds to the sequence from (a) within the scope of the degeneracy of the genetic code or (c) a nucleotide sequence which hybridizes with the sequences from (a) and/or (b).

The invention further relates to a vector which contains at least one copy of the abovementioned DNA sequence and to a cell which is transformed with a DNA sequence or a vector as mentioned above. The invention likewise embraces a protein with palatinase activity which is encoded by a DNA sequence as indicated above and which preferably has one of the amino-acid sequences shown in SEQ ID NO. 8 or SEQ ID NO. 16.

The palatinase from P. rubrum shown in SEQ ID NO. 8 differs from known sucrose-cleaving enzymes in that it cleaves the sucrose isomers which are not cleaved by known enzymes, in particular palatinose.

The amino acid sequence shown in SEQ ID NO. 16 comprises a palatinose hydrolase from MX-45, which cleaves palatinose to form fructose and glucose. The gene coding for this enzyme is shown in SEQ ID NO. 15 and is located in the genome of MX-45 on the 5' side of the isomerase gene shown in SEQ ID NO. 13.

The invention is further described by the following sequence listings and figures:

SEQ ID NO. 1 shows the nucleotide sequence of the gene coding for the sucrose isomerase from Protaminobacter rubrum. The sequence coding for the signal peptide terminates at nucleotide No. 99.

SEQ ID NO. 2 shows the N-terminal section of the nucleotide sequence of the gene coding for the sucrose isomerase of Erwinia rhapontici. The sequence coding for the signal peptide terminates at the nucleotide with No. 108.

SEQ ID NO. 3 shows a section of the nucleotide sequence of the gene coding for the sucrose isomerase from the isolate SZ 62.

SEQ ID NO. 4 shows the amino-acid sequence of the sucrose isomerase from Protaminobacter rubrum.

SEQ ID NO. 5 shows the N-terminal section of the amino-acid sequence of the sucrose isomerase from Erwinia rhapontici.

SEQ ID NO. 6 shows a section of the amino-acid sequence of the sucrose isomerase from the isolate SZ 62.

SEQ ID NO. 7 shows the nucleotide sequence for the palatinase gene from Protaminobacter rubrum.

SEQ ID NO. 8 shows the amino-acid sequence of the palatinase from Protaminobacter rubrum.

SEQ ID NO. 9 shows the nucleotide sequence of a variant of the sucrose isomerase gene from P. rubrum.

SEQ ID NO. 10 shows the corresponding amino-acid sequence.

SEQ ID NO. 11 shows the complete nucleotide sequence of the sucrose isomerase gene from SZ 62.

SEQ ID NO. 12 shows the corresponding amino-acid sequence.

SEQ ID NO. 13 shows most of the sucrose isomerase gene from Pseudomonas mesoacidophila (MX-45).

SEQ ID NO. 14 shows the corresponding amino acid sequence.

SEQ ID NO. 15 shows the palatinose hydrolase gene from Pseudomonas mesoacidophila (MX-45).

SEQ ID NO. 16 shows the corresponding amino-acid sequence.

FIG. 1 shows a comparison of the amino-acid sequences of the sucrose isomerases from Protaminobacter rubrum, Erwinia rhapontici and the isolate SZ 62.

Figure 2:
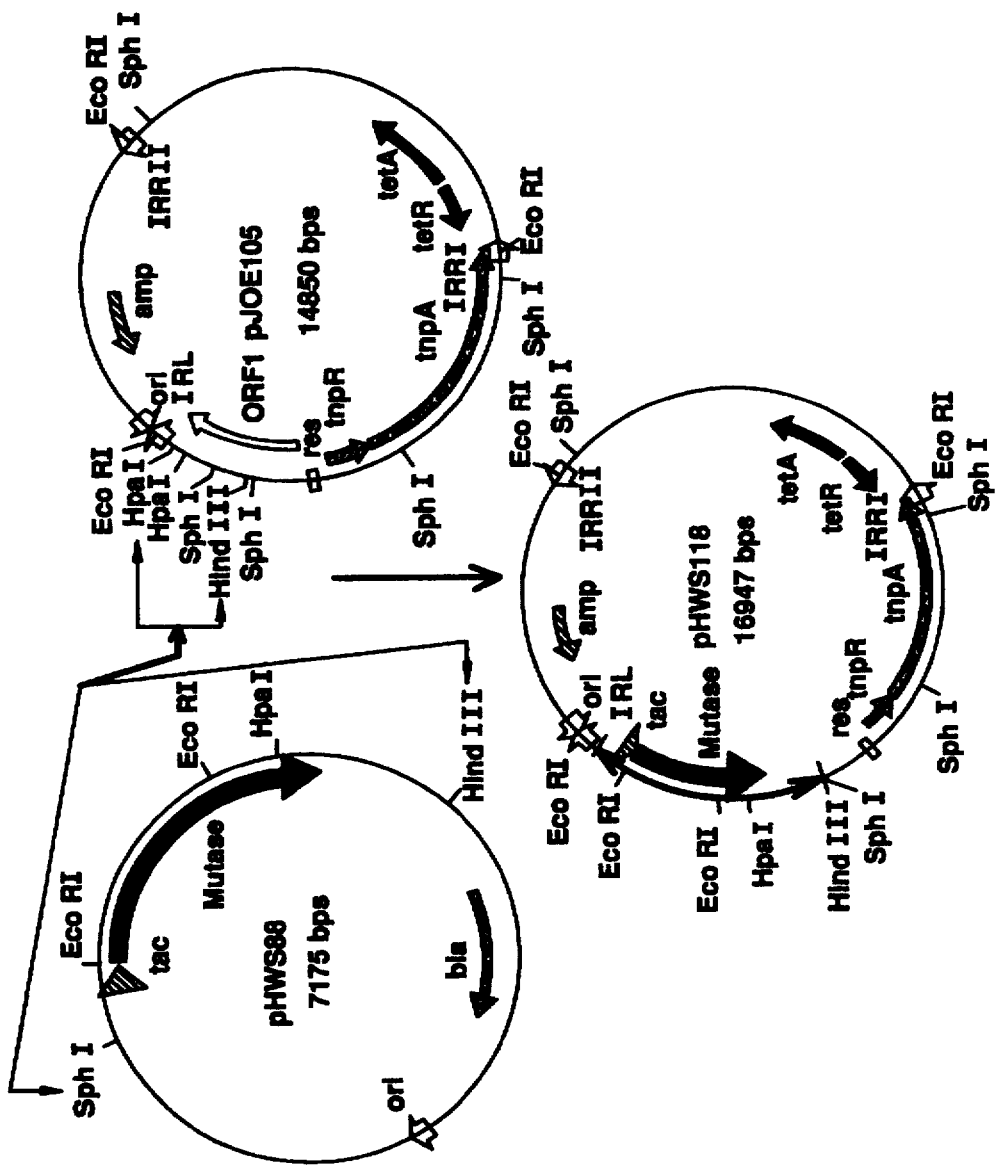
FIG. 2 shows the cloning diagram for the preparation of the recombinant plasmid pEWS 118 which contains the sucrose isomerase gene on the transposon Tn 1721.

The following examples serve to illustrate the present invention.

EXAMPLE 1
Isolation of the sucrose isomerase gene from Protaminobacter rubrum

Complete DNA from the organism Protaminobacter rubrum (CBS 574, 77) was partially digested with Sau3A I. Collections of fragments with a size of about 10 kBp were obtained from the resulting fragment mixture by elution after fractionation by gel electrophoresis and were ligated into a derivative, which had been opened with BamHI, of the lambda EMBL4 vector derivative λ RESII (J. Altenbuchner, Gene 123 (1993), 63–68). A gene bank was produced by transfection of E. coli and transformation of the phages into plasmids according to the above reference. Screening of the kanamycin-resistant colonies in this gene bank was carried out with the radiolabeled oligonucleotide S214 which was derived from the sequence of the N terminus of the mature isomerase by hybridization:

S214: 5'-ATCCCGAAGTGGTGGAAGGAGGC-3' (SEQ ID NO: 21)
         T   A  A         A  A

Subsequently, the plasmid DNA was isolated from the colonies with a positive reaction after appropriate cultivation. After a restriction map had been drawn up, suitable subfragments were sequenced from a plasmid pKAT 01 obtained in this way, and thus the complete nucleotide sequence, which is shown in SEQ ID NO. 1, of the DNA coding for isomerase was obtained. The amino-acid sequence derived therefrom corresponds completely to the peptide sequence of the mature isomerase obtained by sequencing (Edmann degradation). A cleavage site for SacI is located in the non-coding 3' region of this isomerase gene, and a cleavage site for HindIII is located in the non-coding 5' region. This makes it possible to subclone the intact isomerase gene into the vector PUCBM 21 (derivative of the vector pUC 12, Boehringer Mannheim GmbH, Mannheim, Germany) which had previously been cleaved with the said enzymes. The resulting plasmid was called pEWS 34.2 and confers on the E. coli cells harboring it the ability to synthesize sucrose isomerase.

A variant of the sucrose isomerase gene from P. rubrum has the nucleotide sequence shown in SEQ ID NO. 9.

EXAMPLE 2
Cloning and expression of the sucrose isomerase from P. rubrum in E. coli 1. Preparation of the plasmid pHWS88

The non-coding 5' region of the sucrose isomerase gene was deleted from the plasmid pHWS 34.2, using an oligonucleotide S434 with the sequence 5'-CGGAATTCTTATGCCCCGTCAAGGA-3'(SEQ ID NO: 22) , with simultaneous introduction of an EcoRI cleavage site (GAATTC). The isomerase gene derivative obtained in this way was treated with BstE II, the protruding BstE II end was digested off with S1 nuclease and subsequently digestion with EcoRI was carried out. The isomerase gene treated in this way was cloned into the vector pBTacI (Boehringer Mannheim GmbH, Mannheim, Germany) which had been pretreated with EcoRI and SmaI. The resulting vector pHWS 88 (DSM 8824) contains the modified isomerase gene with a preceding EcoRI restriction site in front of the ATG start codon, and the 3' region of the isomerase gene up to the S1-truncated BstE II cleavage site. On induction with IPTG, this vector confers on the cells harboring this plasmid the ability to produce isomerase and resistance to ampicillin (50 to 100 μg/ml). Preferably used for producing isomerase are E. coli host cells which overproduce the lac repressor.

2. Preparation of the plaemid pHWS118::Tn1721Tet

The gene casette for the sucrose mutase was incorporated into a transposon.

This took place by cloning an SphI/HindIII DNA fragment from the plasmid pHWS88, which harbors the sucrose mutase gene under the control of the tac promoter, into the plasmid pJOE105 on which the transposon Tn 1721 is located. The plasmid pJOE105 was deposited on Dec. 16, 1993, at the DSM under the deposit number DSM 8825 in accordance with the provisions of the Budapest Treaty. The resulting plasmid pHWS118, on which the sucrose mutase gene is under the control of the regulatable tac promoter, was used to transform a E. coli strain containing an F' plasmid. FIG. 2 shows the cloning diagram for the preparation of pHWS 118 from pHWS88 and pJOE 105.

Figure 3:
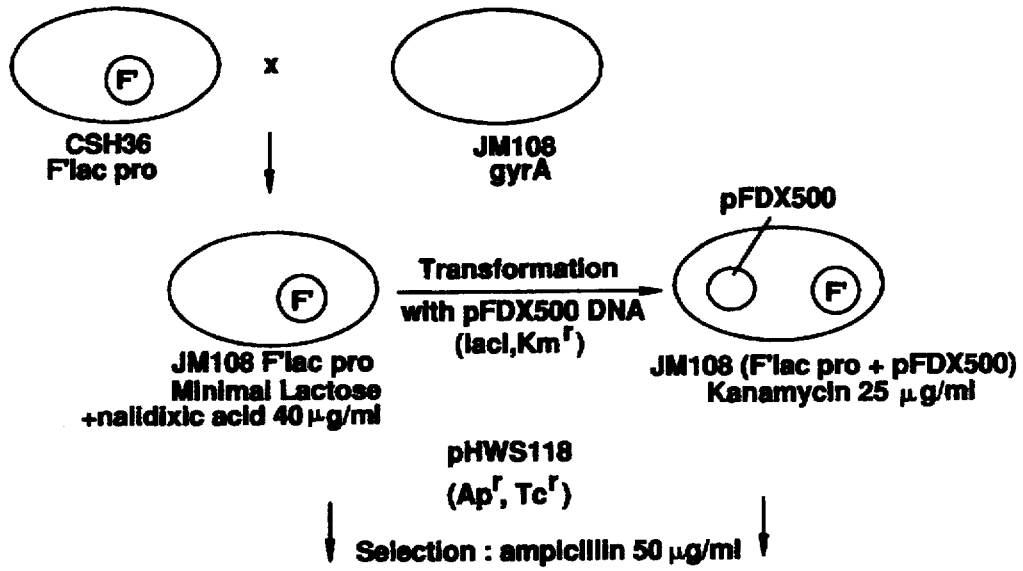
FIG. 3 shows the diagram for the preparation of E. coli transconjugants which contain the sucrose isomerase gene of a F plasmid
Figure 3:
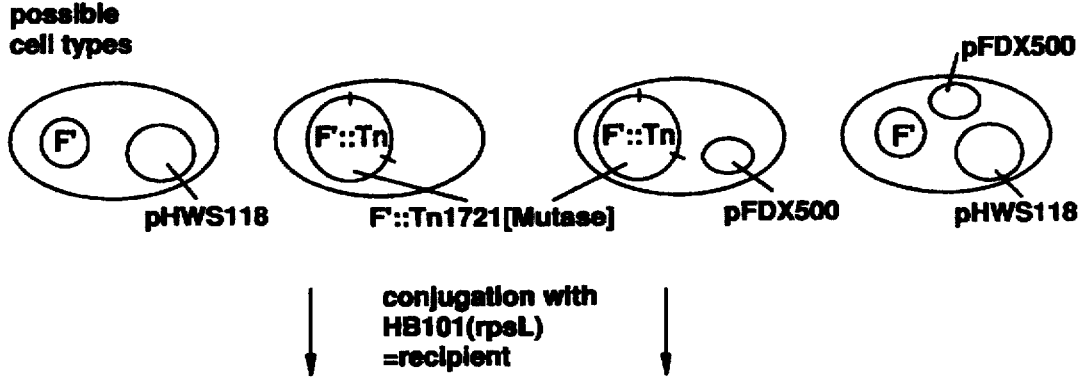
Figure 3:
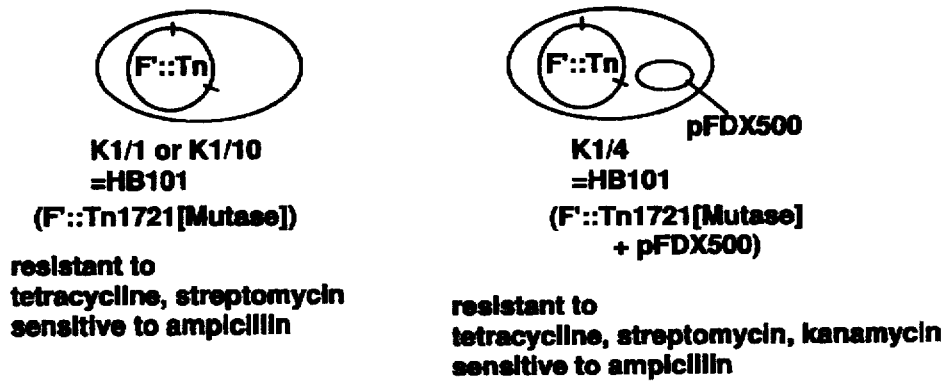

E. coli transconjugants containing the sucrose mutase gene were prepared as described in the diagram in FIG. 3. For this purpose, firstly the F' -harboring E. coli strain CSH36 (J. H. Miller, Experiments in Molecular Genetics, Cold Spring Harbor Laboratory (1972), p. 18), which carries the Lac+ phenotype mediated by the F' plasmid, was crossed with the E. coli strain JM108 which is resistant to nalidixic acid (Sambrook et al., supra, p. A9–A13). Selection on minimal medium to which lactose, proline and nalidixic acid were added resulted in an F'-Lac-harboring transconjugant. This was additionally transformed with the Iq plasmid FDX500 (Brinkmann et al., Gene 85 (1989), 109–114) in order to permit control of the sucrose mutase gene by the tac promoter.

The transconjugant prepared in this way was transformed with the transposon plasmid pHWS118 harboring the sucrose mutase gene. For selection of transconjugants, crossing into the streptomycin-resistant E. coli strain HB101 (Boyer and Roulland-Dussoix, J. Mol. Biol 41 (1969), 459–472) was carried out. Transfer of the tetracycline resistance mediated by the transposon was possible only after transposition of the modified Tn1721Tet from the plasmid pHWS118, which is not capable of conjugation or mobilization, to the F' plasmid which is capable of conjugation. Transmission of the F' plasmid with the modified transposon in HB101 was selected on LB plates containing streptomycin and tetracycline, and retested on ampicillin and nalidixic acid plates.

3. Epression of the sucrose isomerase in E. coli

Examination of the enzyme production by such F' plasmid-harboring E. coli cells showed that it was possible to produce sucrose mutase protein. F' plasmid-containing HB101 cells which harbored no additional Lac repressor plasmid (for example K1/1 or K1/10) produced sucrose mutase protein in identical amounts with and without the inducer isopropyl β-D-thiogalactoside (IPTG). The productivities of three transconjugants K/1, K1/10 and K1/4 are shown in following Table 1.

TABLE 1

| Strain | Surose mutase activity in E. coli HB101 (F'::Tn1721 [Mutase]) | |
|---|---|---|
| | U/mg mutase after 4 hours without induction | U/mg mutase after 4 hours induction with 50 µM IPTG |
| K1/1 | 1.0 | 1.2 |
| K1/10 | 0.9 | 1.1 |
| K1/4 | 0 | 1.6 |

It was possible to observe normal growth of the E. coli cells during production of sucrose mutase protein.

Introduction of the sucrose mutase gene into the F' plasmid in the presence of the repressor-encoded plasmid pFDX500 (see transconjugants K1/4) made it possible to control enzyme production with the inducer IPTG. Whereas no enzymatic activity was measured without IPTG, production of about 1.6 U/mg sucrose mutase protein was obtainable after induction for 4 hours.

No adverse effect on cell growth was observable. The plasmid-harboring E. coli cells reached a density of about 3 $OD_{600}$ after induction for 4 hours.

Up to 1.6 U/mg sucrose mutase activity were measured in transformed E. coli. The synthetic performance is comparable to that of P. rubrum. Analysis of the produced enzyme by SDS gel electrophoresis provides no evidence of inactive protein aggregates. The band of the sucrose mutase protein was only weakly visible with Coomassie staining and was detectable clearly only in a Western blot. It was possible to correlate the strength of the protein band and the measured enzymatic activity in the production of sucrose mutase in E. coli.

EXAMPLE 3

Isolation of the sucrose isomerase gene from Erwinia rhapontici

A gene bank was produced by restriction cleavage of the complete DNA from Erwinia rhapontici (NCPPB 1578) in the same way as described in Example 1.

Using the primer mixtures 5'-TGGTGGAAAGAAGCTGT-3' (SEQ ID NO: 23) and G G 5'-TCCCAGTTCAGGTCCGGCTG-3' (SEQ ID NO: 24) .PCR amplification resulted in A a DNA fragment with whose aid it is possible to identify colonies containing the mutase gene by hybridization.

In this way, a positive clone pSST2023 which contains a fragment, 1305 nucleotides long, of the Erwinia isomerase gene was found. The nucleotide sequence of this fragment is depicted in SEQ ID NO: 2.

Sequence comparison with the Protaminobacter gene reveals an identity of 77.7% and a similarity of 78% for the complete gene section including the signal peptide region, and an identity of 83.4% and a similarity of 90.3% at the amino-acid level.

Figure 1:
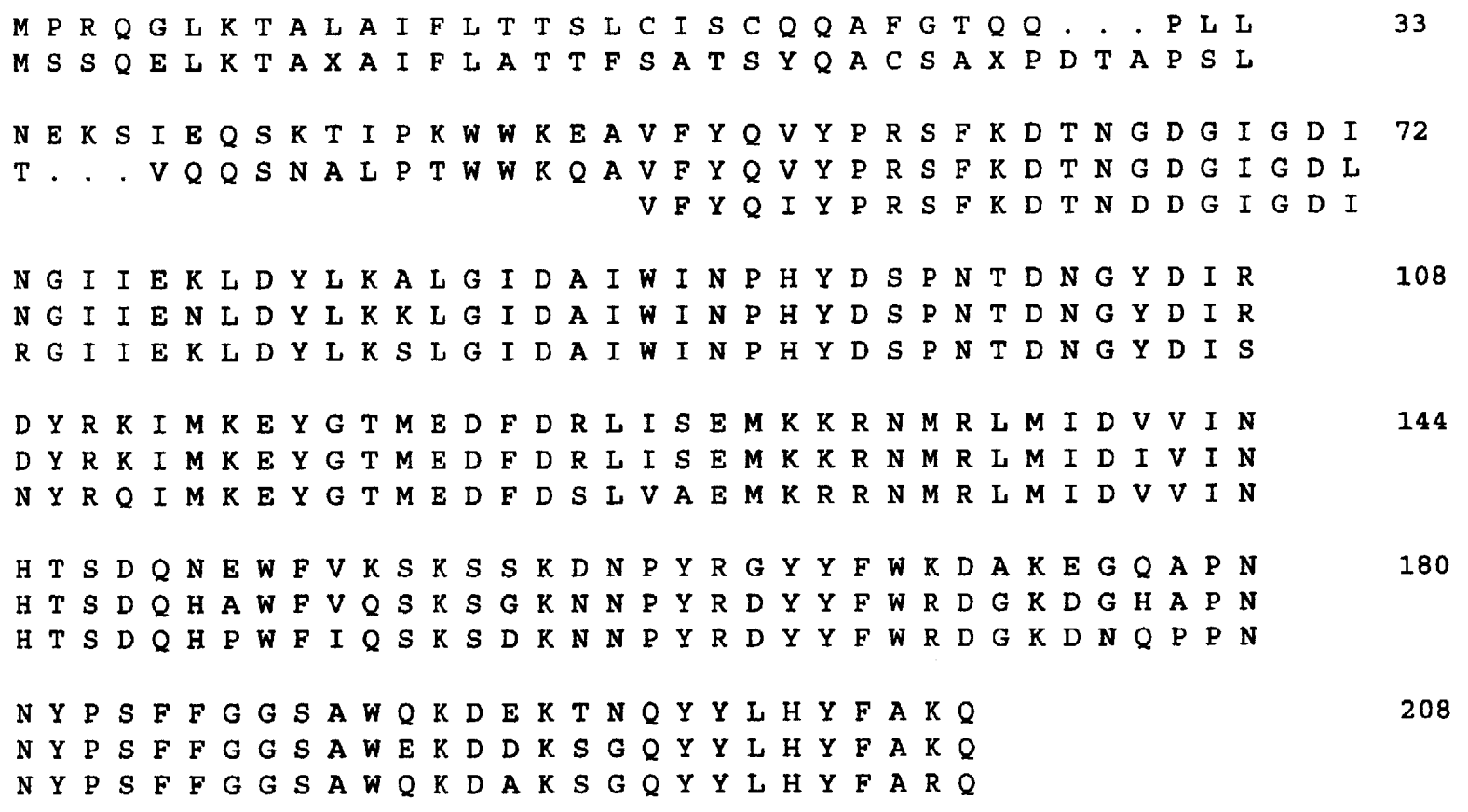

The sequence differences are mainly concentrated in the signal peptide region. For this reason, only the enzyme-encoding region responsible for the actual mutase activity, without the signal peptide, should be considered for comparison. From these viewpoints, the identity or similarity at the nucleotide level emerges as 79%. Comparison of the amino-acid sequences (FIG. 1) in this section shows 87.9% identical amino acids. Of 398 amino acids (this corresponds to 71% of the complete enzyme) in the Erwinia mutase, 349 are the same as in Protaminobacter. 25 of 48 exchanged amino acids show strong similarity so that the overall similarity at the AA level emerges as 94%. The AA exchanges are mainly concentrated in the region between amino acid 141 and 198. In front of this region there is a sequence of 56 conserved amino acids. Other sections also exhibit particularly high conservation (see FIG. 1).

These data show that, for the section cloned and sequenced to date, overall there is very extensive conservation of the two mutases from Erwinia and Protaminobacter.

Identity of the cloned mutase gene from Erwinia

The probe chosen for a rehybridization experiment with genomic Erwinia DNA was the s spI/EcoRI fragment, which is about 500 bp in size, from pSST2023. This fragment was used, after digoxigenin labeling, for hybridization with Erwinia DNA with high stringency (68° C.). Complete Erwinia DNA cut with SspI/EcoRI showed a clear hybridization signal with the expected size of about 500 bp.

Erwinia DNA cut only with SspI showed a hybridization signal of about 2 kb.

It was possible to verify by the successful rehybridization of pSST2023 with genomic Erwinia DNA that the mutase region cloned into pSST2023 originates from *Erwinia rhapontici*.

Cloning of the C-terminal part-fragment of the Erwinia mutase

The N-terminal part-fragment of the Erwinia mutase gene which has been cloned to date has a size of 1.3 kb and has the nucleotide sequence shown in SEQ ID NO. 2. Since it can be assumed that the complete Erwinia gene is virtually identical in size to the known Protaminobacter gene (1.8 kb), a section of about 500 bp is missing from the C-terminal region of the Erwinia gene.

The SspI fragment which is about 2 kb in size from the complete Erwinia DNA was selected for cloning of the Erwinia C-terminus. In a Southern blot, this fragment provides a clear signal with a digoxigenin-labeled DNA probe from pSST2023. This 2 kb SspI fragment overlaps by about 500 bp at the 3' end with the region already cloned in pSST2023. Its size ought to be sufficient for complete cloning of the missing gene section of about 500 bp. The digoxigenin-labeled fragment probe SspI/EcoRI from pSST2023 is suitable for identifying clones which are sought.

EXAMPLE 4
Preparation of a Protaminobacter palatinase-deficient mutant

Figure 4B:
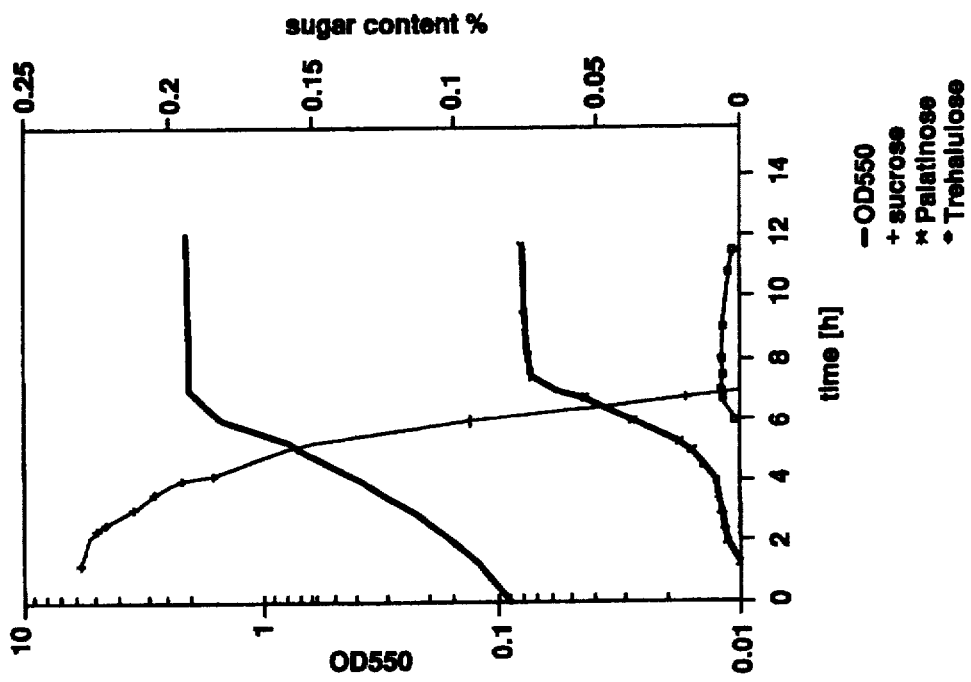
FIG. 4 shows a comparison between the saccharides produced by P. rubrum wild-type cells and cells of the P. rubrum mutant SZZ 13.
Figure 4A:
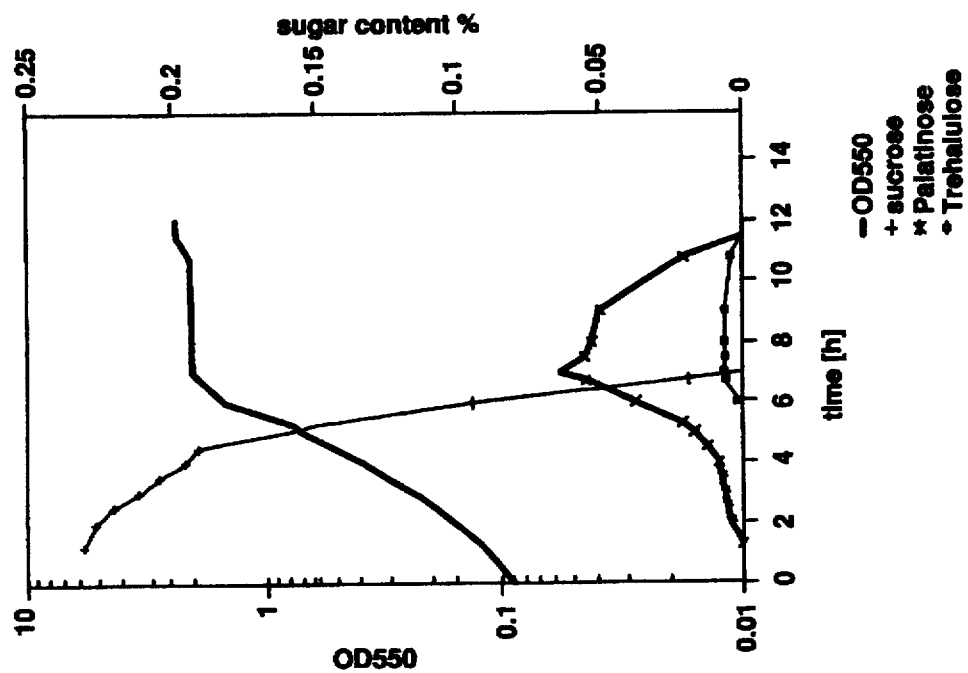

Cells of *Protoaminobacter rubrum* (CBS 547, 77) were mutagenized with N-methyl-N'-nitro-N-nitroso-guanidine by the method of Adelberg et al. (Biochem. Biophys. Research Commun. 18 (1965), 788) as modified by Miller, J., (Experiments in Molecular Genetics, Cold Spring Harbor Laboratory, 125–179 (1972)). Palatinase-deficient mutants were selected using MacConkey palatinose medium (MacConkey Agar Base (Difco Laboratories, Detroit, Mich., USA), 40 g/l with the addition of 20 g/l palatinose, sterilized by filtration, 25 mg/l kanamycin) and minimal salt media (10.5 g of $K_2HPO_4$, 4.5 g of $KH_2PO_4$, 1 g of $(NH_4)_2SO_4$, 0.5 g of sodium citrate, 2 $H_2O$, 0.1 g of $MgSO_4 \cdot 7H_2O$), 1 mg of thiamine, 2 g of palatinose or glucose, 25 mg of kanamycin and 15 g of agar per liter, pH 7.2). Mutants of *P. rubrum* which are white on MacConkey palatinose medium or grow on minimal salt medium with glucose in contrast to the same medium with palatinose are identified as palatinase-deficient mutants. The enzyme activity of cleaving palatinose to glucose and fructose (palatinase activity) cannot, in contrast to the wild-type, be detected in cell extracts from these mutants. On cultivation of these cells in minimal salt medium with 0.2% sucrose as sole C source there is, in contrast to the wild-type cells in which palatinose can be detected only transiently in the time from 4 to 11 hours after starting the culture, a detectable continuous accumulation of palatinose (isomaltulose). Overnight cultures in the same medium contain no palatinose in the case of the wild-type cells but contain >0.08% palatinose in the case of the mutant SZZ 13 (DSM 9121) prepared in this way (see FIG. 4).

EXAMPLE 5
Immobilization of microorganism cells

Cells are rinsed off a subculture of the appropriate strain using 10 ml of a sterile nutrient substrate composed of 8 kg of concentrated juice from a sugar factory (dry matter content=65%), 2 kg of corn steep liquor, 0.1 kg of $(NH_4)_2HPO_4$ and 89.9 kg of distilled water, pH 7.2. This suspension is used as inoculum for preculture in 1 l flasks containing 200 ml of nutrient solution of the above composition in shaking machines. After an incubation time of 30 hours at 29° C., 10 flasks (total contents 2 l) are used to inoculate 18 l of nutrient solution of the above composition in a 30 l small fermenter, and fermentation is carried out at 29° C. and a stirring speed of 350 rpm introducing 20 l of air per minute.

After organism counts above $5 \times 10^9$ organisms per ml are reached, the fermentation is stopped and the cells are harvested from the fermenter solution by centrifugation. The cells are then suspended in a 2% strength sodium alginate solution and immobilized by dropwise addition of the suspension to a 2% strength calcium chloride solution. The resulting immobilizate beads are washed with water and can be stored at +4° C. for several weeks.

Cells of the palatinase-deficient mutant SZZ 13 (DSM 9121) show better catalytic properties in respect of their product composition than do comparable cells from the known microorganisms *Protaminobacter rubrum* (CBS 547, 77) and *Erwinia rhapontici* (NCPPB 1578).

Whole cells and crude extracts of SZZ 13, and an immobilizate of SZZ 13 in calcium alginate prepared as above, were evaluated in respect of product composition in an activity assay. Before the actual activity assay, the immobilizate was swollen in 0.1 mol/l potassium phosphate buffer, pH 6.5.

The activity measurements at 25° C. revealed that no fructose and glucose were found with the mutant SZZ 13, while with *P. rubrum* wild-type cells 2.6% fructose and glucose (based on the total of mono- and disaccharides) were found in whole cells and 12.0% were found in the crude extract. In the case of *E. rhapontici*, 4% glucose and fructose were found in whole cells, and 41% in the crude extract.

EXAMPLE 6
Isolation of the sucrose isomerase gene from other microorganisms

Partial digestion of genomic DNA from the isolate SZ62 (Enterobacter spec.), the organism *Pseudomonas mesoacidophila* (MX-45) or from another microorganism and insertion of the resulting fragments into suitable *E. coli* vectors and transformation result in a gene bank whose clones contain genomic sections between 2 and 15 kb of the donor organism.

Those *E. coli* cells which harbor these plasmids and which display a red coloration of the colony are selected by plating on McConkey palatinose medium. The plasmid DNA contained in these cells is transferred into an *E. coli* mutant which is unable to grow on galactose as sole C source (for example ED 8654, Sambrook et al., supra, pages A9–A13).

This transformed cell line is able to identify palatinose producers in the gene bank which has been prepared as described above from DNA of the donor organism.

To identify the palatinose-producing clones which are sought, the cells of the gene bank are isolated and cultured on minimal salt media containing galactose and sucrose. After replica plating of the colonies on plates containing the same medium, the cells are killed by exposure to toluene vapor. Subsequently, cells of the screening strain are spread as lawn in minimal salt soft agar without added C source over the colonies of the gene bank and incubated. Significant growth of the cells of the screening strain appears only at the location of cells in the gene bank which have produced palatinose. The isomerase content emerges on testing the cells of the replica control.

These *E. coli* clones identified in this way are unable to grow on palatinose as sole C source in the medium, show no

15 ability to cleave sucrose in a test on whole cells or on cell extracts, but on cultivation under these conditions and without addition of sucrose to the medium produce palatinose.

Alternatively, isomerase clones can also be identified using a PCR fragment prepared by the procedure of Example 3.

Use of plasmid DNA from the E. coli clones identified in this way as probes for hybridization on filters with immobilized DNA from the donor organism allows the gene regions which harbor isomerase genes to be detected and specifically made available.

A clone which contains the nucleotide sequence shown in SEQ ID NO. 3, with the amino-acid sequence which is derived therefrom and shown in SEQ ID NO. 6, was identified in this way. In the same way an isomerase clone from DNA of the bacterial strain *Pseudomonas mesoacidophila* MX-45 (FERM 11808) was found.

The complete nucleotide sequence and amino-acid sequence of the sucrose isomerase from SZ 62 are depicted in SEQ ID NO. 11 and 12. A large part of the nucleotide sequence and amino-acid sequence of the sucrose isomerase from MX-45 are depicted in SEQ ID NO. 13 and 14.

EXAMPLE 7
Cloning of a palatinase gene

The *Protaminobacter rubrum* gene bank prepared in Example 1 was screened with the radiolabeled oligonucleotide mixture S433 which was derived from the sequence of the N-terminus of the isolated palatinase and had the sequence CA(G,A)TT(C,T)GG(T,C)TA(C,T)GG-3' (SEQ ID NO: 25).

A positive clone was found, and a plasmid named pKAT 203 was isolated therefrom.

E. coli cells which harbor the plasmid pKAT 203 are able to metabolize palatinose. The cleavage of palatinose to glucose and fructose which is detectable in the activity assay suggests that there is a "palatinase".

It is possible by sequencing pKAT203 DNA with the oligonucleotide S433 as primer to obtain a DNA sequence from which it was possible to read off, after translation into amino-acid sequence data, the N-terminal amino acids known to us. An open reading frame was obtained by a subsequent sequencing step.

Determination of the sequence of the "palatinase" gene

For further sequencing of the "palatinase" gene, part-fragments from the plasmid pKAT 203 were selected on the basis of the restriction map and subcloned in the M13 phage system, and a sequencing of the single-stranded phage DNA was carried out with the universal primer 5'-GTTTTCCCAGTCACGAC-3' (SEQ ID NO: 26).

Combination of the resulting DNA sequence data for the individual fragments taking account of overlapping regions allows a continuous reading frame of 1360 base pairs to be determined for the "palatinase" (SEQ ID NO. 7).

Translation of this DNA sequence into amino-acid data reveals a protein with 453 amino acids (SEQ ID NO. 8) and a molecular weight, which can be deduced therefrom, of about 50,000 Da. This is consistent with the finding that a protein fraction which had a band at about 48,000 Da in the SDS gel was obtainable by concentration of the "palatinase" activity. In the native gel, the palatinose-cleaving activity was attributable to a band with a size of about 150,000 Da.

Comparisons of homology with other known proteins

Comparison of the amino-acid sequence derivable from the DNA sequence with data stored in a gene bank (SwissProt) revealed a homology with melibiase from *E. coli* (MelA) (in two parts: identity 32%).

EXAMPLE 8
Cloning of a palatinose hydrolase gene from *P. mesoacidophila* MX-45

A gene with the nucleotide sequence shown in SEQ ID NO. 15 was isolated from the gene bank prepared from the microorganism *P. mesoacidophila* MX-45 in Example 6. This gene codes for a protein with the amino-acid sequence shown in SEQ ID NO. 16. The protein is a palatinose hydrolase which catalyzes the cleavage of palatinose to form fructose and glucose.

---

What is claimed is:

1. Isolated DNA that codes for a protein with a sucrose isomerase activity and comprising
    (a) a nucleotide sequence selected from the group consisting of SEQ ID NO:1, SEQ ID NO:2, SEQ ID NO:3, SEQ ID NO:9, SEQ ID NO:11, SEQ ID NO:13, and any of these sequences without the signal peptide-coding region;
    (b) a nucleotide sequence corresponding to the sequences from (a) within the scope of the degeneracy of the genetic code, or
    (c) a nucleotide sequence that hybridizes with a sequence from (a), (b), or both (a) and (b); wherein a positive hybridization signal is still observed after washing with 1×SSC and 0.1% SDS at 55° C. for one hour.

2. DNA as claimed in claim 1, wherein the DNA comprises a nucleotide sequence selected from the group consisting of SEQ ID NO:1, SEQ ID NO:2, SEQ ID NO:3, SEQ ID NO:9, SEQ ID NO:11, SEQ ID NO:13, a sequence corresponding to SEQ ID NO:1, SEQ ID NO:2, SEQ ID NO:3, SEQ ID NO:9,SEQ ID NO:11, or SEQ ID NO:13 within the scope of the degeneracy of the genetic code, and any one of these sequences without the signal peptide-coding region.

3. DNA as claimed in claim 1, wherein the nucleotide sequence of the DNA comprises at least one of:
    (a) nucleotides 139 to 155 or
    (b) nucleotides 625 to 644 of the nucleotide sequence shown in SEQ ID NO:1 and
    (c) sequences corresponding to the sequences from (a) and (b) within the scope of the degeneracy of the genetic code.

4. DNA as claimed in claim 1, wherein the nucleotide sequence of the DNA comprises at least one of:
    (a) nucleotides 995 to 1013 or
    (b) nucleotides 1078 to 1094 of the nucleotide sequence shown in SEQ ID NO:1 and
    (c) a sequence corresponding to sequences (a) or (b) within the scope of the degeneracy of the genetic code.

5. An isolated vector that contains at least one copy of a DNA sequence as claimed in claim 1.

6. The vector as claimed in claim 5, wherein the vector is a prokaryotic vector.

7. A host cell transformed with a vector as claimed in claim 6, wherein the vector is present in the host cell with a copy number of less than 10.

8. The vector as claimed in claim 5, wherein the vector contains the sucrose isomerase gene under the control of a regulatable promoter.

9. The vector as claimed in claim 5, wherein the vector is a circular plasmid.

10. The vector as claimed in claim 9, wherein the vector contains the sucrose isomerase gene under the control of a regulatable promoter.

11. A host cell transformed with a vector as claimed in claim 5.

12. A host cell transformed with a DNA sequence as claimed in claim 1.

13. A cell as claimed in claim 12, wherein the cell is a prokaryotic cell.

14. A cell as claimed in claim 13, wherein the cell is a Gram-negative prokaryotic cell.

15. A cell as claimed in claim 13, wherein the cell is an enterobacterial cell.

16. A cell as claimed in claim 13, wherein the cell is an *Escherichia coli* cell, a *Protaminobacter rubrum* cell, or an *Erwinia rhapontici* cell.

17. The plasmid pHWS 88 (DSM 8824).

18. A host cell that contains at least one DNA sequence coding for a protein with a sucrose isomerase activity wherein the DNA has (a) a nucleotide sequence selected from the group consisting of SEQ ID NO:1, SEQ ID NO:2, SEQ ID NO:3, SEQ ID NO:9, SEQ ID NO:11, SEQ ID NO:13, and any of these sequences without the signal peptide-coding region;

(b) a nucleotide sequence corresponding to a sequence from (a) within the scope of the degeneracy of the genetic code, or (c) a nucleotide sequence that hybridizes with a sequence from (a), (b), or both (a) and (b); wherein a positive hybridization signal is still observed after washing with 1×SSC and 0.1% SDS at 55° C. for one hour, and wherein the cell has a reduced palatinose and/or trehalulose metabolism.

19. A host cell as claimed in claim 18, wherein the reduction of the palatinose and/or trehalulose metabolism in the cell takes place by partial or complete inhibition of the expression of invertase and/or palatinase genes.

20. *Protaminobacter rubrum* mutant SZZ 13 (DSM 9121).

21. A method for isolating the DNA of claim 1, wherein said DNA codes for a protein with a sucrose isomerase activity comprising the steps of (a) preparing a gene bank from a donor organism that contains a DNA sequence coding for a protein with a sucrose isomerase activity in a suitable host organism, (b) screening the clones of the gene bank, and (c) isolating the clones which contain a DNA coding for a protein with sucrose isomerase activity.

22. A process as claimed in claim 21, wherein *E. coli* is used as host organism.

23. A process as claimed in claim 21, wherein the steps of preparing a gene bank, screening the clones, and isolating the clones are performed in an *E. coli* strain that does not utilize galactose.

24. A process as claimed in claim 21, wherein the clones in the gene bank are screened using nucleic acid probes that are derived from the sequences shown in SEQ ID NO:1, SEQ ID NO:2, SEQ ID NO:3, SEQ ID NO:9, SEQ ID NO:11, or SEQ ID NO:13.

25. A process as claimed in claim 24, wherein a DNA fragment which has been obtained by PCR amplification of the DNA from the donor organism using the oligonucleotide mixtures 5'-TGGTGGAA(A,G)GA(A,G)GCTGT-3' (SEQ ID NO:17) and 5'-TCCCAGTTCAG(A,G)TCCGGCTG-3' (SEQ ID NO:18) as primers is used as a nucleic acid probe.

26. Isolated DNA that codes for a protein with palatinase activity, trehalulase activity, or both, and comprises (a) one of the nucleotide sequences shown in SEQ ID NO:7 or SEQ ID NO:15, (b) a nucleotide sequence characterized in that it corresponds to the sequence from (a) within the scope of the degeneracy of the genetic code or (c) a nucleotide sequence characterized in that it hybridizes with the sequences from (a), (b), or both (a) and (b); wherein a positive hybridization signal is still observed after washing with 1×SSC and 0.1% SDS at 55° C. for one hour.

27. An isolated vector that contains at least one copy of a DNA sequence as claimed in claim 26.

28. A host cell transformed with a DNA sequence as claimed in claim 26.

29. A host cell transformed with a vector as claimed in claim 27.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
      ( A ) LENGTH: 1890 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:1:

```
ATGCCCCGTC  AAGGATTGAA  AACTGCACTA  GCGATTTTTC  TAACCACATC  ATTATGCATC      60

TCATGCCAGC  AAGCCTTCGG  TACGCAACAA  CCCTTGCTTA  ACGAAAAGAG  TATCGAACAG     120

TCGAAAACCA  TACCTAAATG  GTGGAAGGAG  GCTGTTTTTT  ATCAGGTGTA  TCCGCGCTCC     180

TTTAAAGACA  CCAACGGAGA  TGGCATCGGG  GATATTAACG  GCATCATAGA  AAAATTAGAC     240

TATCTAAAAG  CCTTGGGGAT  TGATGCCATT  TGGATCAACC  CACATTATGA  TTCTCCGAAC     300
```

-continued

```
ACGGATAATG GTTACGATAT ACGTGATTAT CGAAAAATCA TGAAAGAATA TGGCACGATG    360
GAGGATTTTG ACCGCCTGAT TTCTGAAATG AAAAACGGA ATATGCGGTT GATGATTGAT    420
GTGGTCATCA ACCACACCAG CGATCAAAAC GAATGGTTTG TTAAAAGTAA AAGCAGTAAG   480
GATAATCCTT ATCGCGGCTA TTATTCTGG AAAGATGCTA AAGAAGGGCA GGCGCCTAAT    540
AATTACCCTT CATTCTTTGG TGGCTCGGCG TGGCAAAAAG ATGAAAGAC CAATCAATAC    600
TACCTGCACT ATTTTGCTAA ACAACAGCCT GACCTAAACT GGGATAATCC CAAAGTCCGT   660
CAAGATCTTT ATGCAATGTT ACGTTCTGG TTAGATAAAG GCGTGTCTGG TTTACGTTTT    720
GATACGGTAG CGACCTACTC AAAAATTCCG GATTTCCCAA ATCTCACCCA ACAACAGCTG   780
AAGAATTTTG CAGCGGAGTA TACCAAGGGC CCTAATATTC ATCGTTACGT CAATGAAATG   840
AATAAAGAGG TCTTGTCTCA TTACGACATT GCGACTGCCG GTGAAATCTT TGGCGTACCC   900
TTGGATCAAT CGATAAAGTT CTTCGATCGC CGCCGTGATG AGCTGAACAT TGCATTTACC   960
TTTGACTTAA TCAGACTCGA TCGAGACTCT GATCAAAGAT GGCGTCGAAA AGATTGGAAA  1020
TTGTCGCAAT TCCGGCAGAT CATCGATAAC GTTGACCGTA CTGCAGGAGA ATATGGTTGG  1080
AATGCCTTCT TCTTGGATAA CCACGACAAT CCGCGCGCTG TCTCGCACTT TGGCGATGAT  1140
GATCGCCCAC AATGGCGTGA GCCATCGGCT AAAGCGCTTG CAACCTTGAC GCTGACTCAA  1200
CGAGCAACAC CTTTTATTTA TCAAGGTTCA GAATTGGGCA TGACCAATTA CCCGTTTAAA  1260
GCTATTGATG AATTCGATGA TATTGAGGTG AAAGGTTTTT GGCATGACTA CGTTGAGACA  1320
GGAAAGGTCA AAGCCGACGA GTTCTTGCAA AATGTACGCC TGACGAGCAG GGATAACAGC  1380
CGGACGCCGT TCCAATGGGA TGGGAGCAAA AATGCAGGAT TCACGAGCGG AAAACCTTGG  1440
TTCAAGGTCA ACCCAAACTA CCAGGAAATC AATGCAGTAA GTCAAGTCAC ACAACCCGAC  1500
TCAGTATTTA ACTATTATCG TCAGTTGATC AAGATAAGGC ATGACATCCC GGCACTGACC  1560
TATGGTACAT ACACCGATTT GGATCCTGCA AATGATTCGG TCTACGCCTA TACACGCAGC  1620
CTTGGGGCGG AAAAATATCT TGTTGTTGTT AACTTCAAGG AGCAAATGAT GAGATATAAA  1680
TTACCGGATA ATTTATCCAT TGAGAAAGTG ATTATAGACA GCAACAGCAA AAACGTGGTG  1740
AAAAAGAATG ATTCATTACT CGAGCTAAAA CCATGGCAGT CAGGGGTTTA TAAAACTAAA  1800
TCAATAAATC TCATAGTCAC GCCAAATAAT GTAAATATAT TGAAACTATT AAAACCGGCA  1860
TTTTATGCCG GTTTTTTTAG CGCAAAATAG                                    1890
```

( 2 ) INFORMATION FOR SEQ ID NO:2:

( i ) SEQUENCE CHARACTERISTICS:
        ( A ) LENGTH: 1305 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_RNA
        ( B ) LOCATION: 28
        ( D ) OTHER INFORMATION: /note= "N = Unknown"

( i x ) FEATURE:
        ( A ) NAME/KEY: misc_RNA
        ( B ) LOCATION: 85..87
        ( D ) OTHER INFORMATION: /note= "N = Unknown"

( x i ) SEQUENCE DESCRIPTION: SEQ ID NO:2:

```
ATGTCCTCTC AAGGATTGAA AACGGCTNTC GCTATTTTTC TTGCAACCAC TTTTTCTGCC    60
```

-continued

```
ACATCCTATC AGGCCTGCAG TGCCNNNCCA GATACCGCCC CCTCACTCAC CGTTCAGCAA    120
TCAAATGCCC TGCCCACATG GTGGAAGCAG GCTGTTTTTT ATCAGGTATA TCCACGCTCA    180
TTTAAAGATA CGAATGGGGA TGGCATTGGG GATTTAAACG GTATTATTGA GAATTTAGAC    240
TATCTGAAGA AACTGGGTAT TGATGCGATT TGGATCAATC CACATTACGA TTCGCCGAAT    300
ACGGATAATG GTTATGACAT CCGGGATTAC CGTAAGATAA TGAAAGAATA CGGTACGATG    360
GAAGACTTTG ACCGTCTTAT TTCAGAAATG AAGAAACGCA ATATGCGTTT GATGATTGAT    420
ATTGTTATCA ACCACACCAG CGATCAGCAT GCCTGGTTTG TTCAGAGCAA ATCGGGTAAG    480
AACAACCCCT ACAGGGACTA TTACTTCTGG CGTGACGGTA AGGATGGCCA TGCCCCCAAT    540
AACTATCCCT CCTTCTTCGG TGGCTCAGCC TGGGAAAAAG ACGATAAATC AGGCCAGTAT    600
TACCTCCATT ACTTTGCCAA ACAGCAACCC GACCTCAACT GGGACAATCC CAAAGTCCGT    660
CAAGACCTGT ATGACATGCT CCGCTTCTGG TTAGATAAAG GCGTTTCTGG TTTACGCTTT    720
GATACCGTTG CCACCTACTC GAAAATCCCG AACTTCCCTG ACCTTAGCCA ACAGCAGTTA    780
AAAAATTTCG CCGAGGAATA TACTAAAGGT CCTAAAATTC ACGACTACGT GAATGAAATG    840
AACAGAGAAG TATTATCCCA CTATGATATC GCCACTGCGG GGGAAATATT TGGGGTTCCT    900
CTGGATAAAT CGATTAAGTT TTTCGATCGC CGTAGAAATG AATTAAATAT AGCGTTTACG    960
TTTGATCTGA TCAGGCTCGA TCGTGATGCT GATGAAAGAT GGCGGCGAAA AGACTGGACC   1020
CTTTCGCAGT TCCGAAAAAT TGTCGATAAG GTTGACCAAA CGGCAGGAGA GTATGGGTGG   1080
AATGCCTTTT TCTTAGACAA TCACGACAAT CCCCGCGCGG TTTCTCACTT TGGTGATGAT   1140
CGACCACAAT GGCGCGAGCA TGCGGCGAAA GCACTGGCAA CATTGACGCT GACCCAGCGT   1200
GCAACGCCGT TTATCTATCA GGGTTCAGAA CTCGGTATGA CCAATTATCC CTTTAAAAAA   1260
ATCGATGATT TCGATGATGT AGAGGTGAAA GGTTTTTGGC AAGAC                   1305
```

( 2 ) INFORMATION FOR SEQ ID NO:3:

( i ) SEQUENCE CHARACTERISTICS:
        ( A ) LENGTH: 471 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
GTTTTTTATC AGATCTATCC TCGCTCATTT AAAGACACCA ATGATGATGG CATTGGCGAT    60
ATTCGCGGTA TTATTGAAAA GCTGGACTAT CTGAAATCGC TCGGTATTGA CGCTATCTGG   120
ATCAATCCCC ATTACGACTC TCCGAACACC GATAACGGCT ATGACATCAG TAATTATCGT   180
CAGATAATGA AAGAGTATGG CACAATGGAG GATTTTGATA GCCTTGTTGC CGAAATGAAA   240
AAACGAAATA TGCGCTTAAT GATCGACGTG GTCATTAACC ATACCAGTGA TCAACACCCG   300
TGGTTTATTC AGAGTAAAAG CGATAAAAAC AACCCTTATC GTGACTATTA TTTCTGGCGT   360
GACGGAAAAG ATAATCAGCC ACCTAATAAT TACCCCTCAT TTTTCGGCGG CTCGGCATGG   420
CAAAAAGATG CAAAGTCAGG ACAGTACTAT TTACACTATT TTGCCAGACA G             471
```

( 2 ) INFORMATION FOR SEQ ID NO:4:

( i ) SEQUENCE CHARACTERISTICS:
        ( A ) LENGTH: 629 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

| Met | Pro | Arg | Gln | Gly | Leu | Lys | Thr | Ala | Leu | Ala | Ile | Phe | Leu | Thr | Thr |
|---|---|---|---|---|---|---|---|---|---|---|---|---|---|---|---|
| 1 | | | | 5 | | | | | 10 | | | | | 15 | |
| Ser | Leu | Cys | Ile | Ser | Cys | Gln | Gln | Ala | Phe | Gly | Thr | Gln | Gln | Pro | Leu |
| | | | 20 | | | | | 25 | | | | | 30 | | |
| Leu | Asn | Glu | Lys | Ser | Ile | Glu | Gln | Ser | Lys | Thr | Ile | Pro | Lys | Trp | Trp |
| | | 35 | | | | | 40 | | | | | 45 | | | |
| Lys | Glu | Ala | Val | Phe | Tyr | Gln | Val | Tyr | Pro | Arg | Ser | Phe | Lys | Asp | Thr |
| | 50 | | | | | 55 | | | | | 60 | | | | |
| Asn | Gly | Asp | Gly | Ile | Gly | Asp | Ile | Asn | Gly | Ile | Ile | Glu | Lys | Leu | Asp |
| 65 | | | | | 70 | | | | | 75 | | | | | 80 |
| Tyr | Leu | Lys | Ala | Leu | Gly | Ile | Asp | Ala | Ile | Trp | Ile | Asn | Pro | His | Tyr |
| | | | | 85 | | | | | 90 | | | | | 95 | |
| Asp | Ser | Pro | Asn | Thr | Asp | Asn | Gly | Tyr | Asp | Ile | Arg | Asp | Tyr | Arg | Lys |
| | | | 100 | | | | | 105 | | | | | 110 | | |
| Ile | Met | Lys | Glu | Tyr | Gly | Thr | Met | Glu | Asp | Phe | Asp | Arg | Leu | Ile | Ser |
| | | 115 | | | | | 120 | | | | | 125 | | | |
| Glu | Met | Lys | Lys | Arg | Asn | Met | Arg | Leu | Met | Ile | Asp | Val | Val | Ile | Asn |
| | 130 | | | | | 135 | | | | | 140 | | | | |
| His | Thr | Ser | Asp | Gln | Asn | Glu | Trp | Phe | Val | Lys | Ser | Lys | Ser | Ser | Lys |
| 145 | | | | | 150 | | | | | 155 | | | | | 160 |
| Asp | Asn | Pro | Tyr | Arg | Gly | Tyr | Tyr | Phe | Trp | Lys | Asp | Ala | Lys | Glu | Gly |
| | | | | 165 | | | | | 170 | | | | | 175 | |
| Gln | Ala | Pro | Asn | Asn | Tyr | Pro | Ser | Phe | Phe | Gly | Gly | Ser | Ala | Trp | Gln |
| | | | 180 | | | | | 185 | | | | | 190 | | |
| Lys | Asp | Glu | Lys | Thr | Asn | Gln | Tyr | Tyr | Leu | His | Tyr | Phe | Ala | Lys | Gln |
| | | 195 | | | | | 200 | | | | | 205 | | | |
| Gln | Pro | Asp | Leu | Asn | Trp | Asp | Asn | Pro | Lys | Val | Arg | Gln | Asp | Leu | Tyr |
| | 210 | | | | | 215 | | | | | 220 | | | | |
| Ala | Met | Leu | Arg | Phe | Trp | Leu | Asp | Lys | Gly | Val | Ser | Gly | Leu | Arg | Phe |
| 225 | | | | | 230 | | | | | 235 | | | | | 240 |
| Asp | Thr | Val | Ala | Thr | Tyr | Ser | Lys | Ile | Pro | Asp | Phe | Pro | Asn | Leu | Thr |
| | | | | 245 | | | | | 250 | | | | | 255 | |
| Gln | Gln | Gln | Leu | Lys | Asn | Phe | Ala | Ala | Glu | Tyr | Thr | Lys | Gly | Pro | Asn |
| | | | 260 | | | | | 265 | | | | | 270 | | |
| Ile | His | Arg | Tyr | Val | Asn | Glu | Met | Asn | Lys | Glu | Val | Leu | Ser | His | Tyr |
| | | 275 | | | | | 280 | | | | | 285 | | | |
| Asp | Ile | Ala | Thr | Ala | Gly | Glu | Ile | Phe | Gly | Val | Pro | Leu | Asp | Gln | Ser |
| | 290 | | | | | 295 | | | | | 300 | | | | |
| Ile | Lys | Phe | Phe | Asp | Arg | Arg | Arg | Asp | Glu | Leu | Asn | Ile | Ala | Phe | Thr |
| 305 | | | | | 310 | | | | | 315 | | | | | 320 |
| Phe | Asp | Leu | Ile | Arg | Leu | Asp | Arg | Asp | Ser | Asp | Gln | Arg | Trp | Arg | Arg |
| | | | | 325 | | | | | 330 | | | | | 335 | |
| Lys | Asp | Trp | Lys | Leu | Ser | Gln | Phe | Arg | Gln | Ile | Ile | Asp | Asn | Val | Asp |
| | | | 340 | | | | | 345 | | | | | 350 | | |
| Arg | Thr | Ala | Gly | Glu | Tyr | Gly | Trp | Asn | Ala | Phe | Phe | Leu | Asp | Asn | His |
| | | 355 | | | | | 360 | | | | | 365 | | | |
| Asp | Asn | Pro | Arg | Ala | Val | Ser | His | Phe | Gly | Asp | Asp | Arg | Pro | Gln |
| | 370 | | | | | 375 | | | | | 380 | | | | |
| Trp | Arg | Glu | Pro | Ser | Ala | Lys | Ala | Leu | Ala | Thr | Leu | Thr | Leu | Thr | Gln |
| 385 | | | | | 390 | | | | | 395 | | | | | 400 |
| Arg | Ala | Thr | Pro | Phe | Ile | Tyr | Gln | Gly | Ser | Glu | Leu | Gly | Met | Thr | Asn |

|   |   |   |   | 405 |   |   |   | 410 |   |   |   | 415 |   |   |
|---|---|---|---|---|---|---|---|---|---|---|---|---|---|---|
| Tyr | Pro | Phe | Lys<br>420 | Ala | Ile | Asp | Glu | Phe<br>425 | Asp | Asp | Ile | Glu | Val<br>430 | Lys | Gly |
| Phe | Trp | His<br>435 | Asp | Tyr | Val | Glu | Thr<br>440 | Gly | Lys | Val | Lys | Ala<br>445 | Asp | Glu | Phe |
| Leu | Gln<br>450 | Asn | Val | Arg | Leu | Thr<br>455 | Ser | Arg | Asp | Asn | Ser<br>460 | Arg | Thr | Pro | Phe |
| Gln<br>465 | Trp | Asp | Gly | Ser<br>470 | Lys | Asn | Ala | Gly | Phe<br>475 | Thr | Ser | Gly | Lys | Pro | Trp<br>480 |
| Phe | Lys | Val | Asn | Pro<br>485 | Asn | Tyr | Gln | Glu | Ile<br>490 | Asn | Ala | Val | Ser | Gln<br>495 | Val |
| Thr | Gln | Pro | Asp<br>500 | Ser | Val | Phe | Asn | Tyr<br>505 | Tyr | Arg | Gln | Leu | Ile<br>510 | Lys | Ile |
| Arg | His | Asp<br>515 | Ile | Pro | Ala | Leu | Thr<br>520 | Tyr | Gly | Thr | Tyr | Thr<br>525 | Asp | Leu | Asp |
| Pro | Ala<br>530 | Asn | Asp | Ser | Val<br>535 | Tyr | Ala | Tyr | Thr | Arg | Ser<br>540 | Leu | Gly | Ala | Glu |
| Lys<br>545 | Tyr | Leu | Val | Val | Val<br>550 | Asn | Phe | Lys | Glu | Gln<br>555 | Met | Met | Arg | Tyr | Lys<br>560 |
| Leu | Pro | Asp | Asn | Leu<br>565 | Ser | Ile | Glu | Lys | Val<br>570 | Ile | Ile | Asp | Ser | Asn<br>575 | Ser |
| Lys | Asn | Val | Val<br>580 | Lys | Lys | Asn | Asp | Ser<br>585 | Leu | Leu | Glu | Leu | Lys<br>590 | Pro | Trp |
| Gln | Ser | Gly<br>595 | Val | Tyr | Lys | Thr | Lys<br>600 | Ser | Ile | Asn | Leu | Ile<br>605 | Val | Thr | Pro |
| Asn | Asn<br>610 | Val | Asn | Ile | Leu | Lys<br>615 | Leu | Leu | Lys | Pro | Ala<br>620 | Phe | Tyr | Ala | Gly |
| Phe<br>625 | Phe | Ser | Ala | Lys |   |   |   |   |   |   |   |   |   |   |   |

(2) INFORMATION FOR SEQ ID NO:5:

(i) SEQUENCE CHARACTERISTICS:
        (A) LENGTH: 435 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 10
        (D) OTHER INFORMATION: /note= "X = Unknown"

(ix) FEATURE:
        (A) NAME/KEY: Peptide
        (B) LOCATION: 29
        (D) OTHER INFORMATION: /note= "X = Unknown"

(xi) SEQUENCE DESCRIPTION: SEQ ID NO:5:

| Met<br>1 | Ser | Ser | Gln | Gly<br>5 | Leu | Lys | Thr | Ala | Xaa<br>10 | Ala | Ile | Phe | Leu | Ala<br>15 | Thr |
|---|---|---|---|---|---|---|---|---|---|---|---|---|---|---|---|
| Thr | Phe | Ser | Ala<br>20 | Thr | Ser | Tyr | Gln | Ala<br>25 | Cys | Ser | Ala | Xaa | Pro<br>30 | Asp | Thr |
| Ala | Pro | Ser | Leu | Thr<br>35 | Val | Gln | Gln | Ser | Asn<br>40 | Ala | Leu | Pro | Thr<br>45 | Trp | Trp |
| Lys | Gln<br>50 | Ala | Val | Phe | Tyr | Gln<br>55 | Val | Tyr | Pro | Arg | Ser<br>60 | Phe | Lys | Asp | Thr |
| Asn | Gly | Asp | Gly | Ile | Gly | Asp | Leu | Asn | Gly | Ile | Ile | Glu | Asn | Leu | Asp |

65                              70                              75                              80
Tyr  Leu  Lys  Lys  Leu  Gly  Ile  Asp  Ala  Ile  Trp  Ile  Asn  Pro  His  Tyr
                         85                              90                              95

Asp  Ser  Pro  Asn  Thr  Asp  Asn  Gly  Tyr  Asp  Ile  Arg  Asp  Tyr  Arg  Lys
                    100                            105                            110

Ile  Met  Lys  Glu  Tyr  Gly  Thr  Met  Glu  Asp  Phe  Asp  Arg  Leu  Ile  Ser
               115                            120                            125

Glu  Met  Lys  Lys  Arg  Asn  Met  Arg  Leu  Met  Ile  Asp  Ile  Val  Ile  Asn
          130                            135                            140

His  Thr  Ser  Asp  Gln  His  Ala  Trp  Phe  Val  Gln  Ser  Lys  Ser  Gly  Lys
145                      150                            155                            160

Asn  Asn  Pro  Tyr  Arg  Asp  Tyr  Tyr  Phe  Trp  Arg  Asp  Gly  Lys  Asp  Gly
                    165                            170                            175

His  Ala  Pro  Asn  Asn  Tyr  Pro  Ser  Phe  Phe  Gly  Gly  Ser  Ala  Trp  Glu
               180                            185                            190

Lys  Asp  Asp  Lys  Ser  Gly  Gln  Tyr  Tyr  Leu  His  Tyr  Phe  Ala  Lys  Gln
          195                            200                            205

Gln  Pro  Asp  Leu  Asn  Trp  Asp  Asn  Pro  Lys  Val  Arg  Gln  Asp  Leu  Tyr
     210                            215                            220

Asp  Met  Leu  Arg  Phe  Trp  Leu  Asp  Lys  Gly  Val  Ser  Gly  Leu  Arg  Phe
225                      230                            235                            240

Asp  Thr  Val  Ala  Thr  Tyr  Ser  Lys  Ile  Pro  Asn  Phe  Pro  Asp  Leu  Ser
                    245                            250                            255

Gln  Gln  Gln  Leu  Lys  Asn  Phe  Ala  Glu  Glu  Tyr  Thr  Lys  Gly  Pro  Lys
               260                            265                            270

Ile  His  Asp  Tyr  Val  Asn  Glu  Met  Asn  Arg  Glu  Val  Leu  Ser  His  Tyr
          275                            280                            285

Asp  Ile  Ala  Thr  Ala  Gly  Glu  Ile  Phe  Gly  Val  Pro  Leu  Asp  Lys  Ser
290                      295                            300

Ile  Lys  Phe  Phe  Asp  Arg  Arg  Arg  Asn  Glu  Leu  Asn  Ile  Ala  Phe  Thr
305                      310                            315                            320

Phe  Asp  Leu  Ile  Arg  Leu  Asp  Arg  Asp  Ala  Asp  Glu  Arg  Trp  Arg  Arg
                    325                            330                            335

Lys  Asp  Trp  Thr  Leu  Ser  Gln  Phe  Arg  Lys  Ile  Val  Asp  Lys  Val  Asp
               340                            345                            350

Gln  Thr  Ala  Gly  Glu  Tyr  Gly  Trp  Asn  Ala  Phe  Phe  Leu  Asp  Asn  His
          355                            360                            365

Asp  Asn  Pro  Arg  Ala  Val  Ser  His  Phe  Gly  Asp  Asp  Arg  Pro  Gln  Trp
     370                            375                            380

Arg  Glu  His  Ala  Ala  Lys  Ala  Leu  Ala  Thr  Leu  Thr  Leu  Thr  Gln  Arg
385                      390                            395                            400

Ala  Thr  Pro  Phe  Ile  Tyr  Gln  Gly  Ser  Glu  Leu  Gly  Met  Thr  Asn  Tyr
                    405                            410                            415

Pro  Phe  Lys  Lys  Ile  Asp  Asp  Phe  Asp  Asp  Val  Glu  Val  Lys  Gly  Phe
               420                            425                            430

Trp  Gln  Asp
          435

( 2 ) INFORMATION FOR SEQ ID NO:6:

( i ) SEQUENCE CHARACTERISTICS:
 ( A ) LENGTH: 157 amino acids
 ( B ) TYPE: amino acid
 ( C ) STRANDEDNESS: single
 ( D ) TOPOLOGY: linear ( i i ) MOLECULE TYPE: peptide ( x i ) SEQUENCE DESCRIPTION: SEQ ID NO:6:

```
Val Phe Tyr Gln Ile Tyr Pro Arg Ser Phe Lys Asp Thr Asn Asp Asp
 1               5                  10                  15
Gly Ile Gly Asp Ile Arg Gly Ile Ile Glu Lys Leu Asp Tyr Leu Lys
                20                  25                  30
Ser Leu Gly Ile Asp Ala Ile Trp Ile Asn Pro His Tyr Asp Ser Pro
            35                  40                  45
Asn Thr Asp Asn Gly Tyr Asp Ile Ser Asn Tyr Arg Gln Ile Met Lys
        50                  55                  60
Glu Tyr Gly Thr Met Glu Asp Phe Asp Ser Leu Val Ala Glu Met Lys
 65                  70                  75                  80
Lys Arg Asn Met Arg Leu Met Ile Asp Val Val Ile Asn His Thr Ser
                85                  90                  95
Asp Gln His Pro Trp Phe Ile Gln Ser Lys Ser Asp Lys Asn Asn Pro
            100                 105                 110
Tyr Arg Asp Tyr Tyr Phe Trp Arg Asp Gly Lys Asp Asn Gln Pro Pro
        115                 120                 125
Asn Asn Tyr Pro Ser Phe Phe Gly Gly Ser Ala Trp Gln Lys Asp Ala
    130                 135                 140
Lys Ser Gly Gln Tyr Tyr Leu His Tyr Phe Ala Arg Gln
145                 150                 155
```

( 2 ) INFORMATION FOR SEQ ID NO:7:

( i ) SEQUENCE CHARACTERISTICS:
  ( A ) LENGTH: 1362 base pairs
  ( B ) TYPE: nucleic acid
  ( C ) STRANDEDNESS: single
  ( D ) TOPOLOGY: linear ( i i ) MOLECULE TYPE: DNA (genomic)

( x i ) SEQUENCE DESCRIPTION: SEQ ID NO:7:

```
ATGGCTACAA AAATCGTTTT AGTGGGCGCA GGCAGCGCGC AATTCGGCTA CGGCACCCTG    60
GGCGATATCT TCCAGAGCAA GACGCTGTAC GGCAGTGAAA TTGTGCTGCA TGACATCAAC   120
CCAACCTCGC TGGCCGTGAC CGAGAAAACC GCCCGTGACT TCCTGGCTGC GGAAGATCTG   180
CCGTTTATCG TCAGCGCCAC CACCGATCGC AAAACCGCGC TGAGCGGAGC GGAGTTCGTG   240
ATTATCTCCA TTGAAGTGGG CGACCGCTTT GCCCTGTGGG ATCTCGACTG GCAGATCCCG   300
CAACAGTATG GCATTCAGCA GGTGTATGGT GAAAACGGTG GCCCTGGCGG GCTGTTCCAC   360
TCGCTGCGCA TCATTCCACC GATCCTCGAC ATCTGCGCCG ACGTGGCGGA CATTTGCCCG   420
AACGCCTGGG TATTCAACTA CTCGAACCCG ATGAGCCGCA TTTGCACCAC CGTGCATCGC   480
CGTTTCCCGC AGCTCAACTT TGTCGGCATG TGCCATGAAA TCGCCTCACT TGAGCGTTAT   540
CTGCCAGAAA TGCTCGGCAC CTCCTTCGAC AATCTCACTC TGCGCGCTGC CGGGCTGAAC   600
CACTTCAGCG TGTTGCTGGA GGCCAGCTAT AAAGACAGCG AAAAGACGC TTACGCCGAC   660
GTACGCGCCA AGGCACCGGA CTATTTCTCC CGTCTGCCGG CGTACAGCGA TATTCTGGCT   720
TACACCCGCA ATCACGGCAA ATTGGTGGAG ACAGAAGGCA GCACCGAACG CGATGCGCTG   780
GGCGGCAAAG ACAGCGCCTA TCCGTGGGCG GACCGCACGC TGTTCAAAGA GATCCTGGAG   840
AAGTTTCACC ATTTGCCGAT CACCGGCGAC AGCCACTTTG GCGAGTACAT CCGTTGGGCC   900
AGCGAAGTCA GCGATCACCG CGGTATCCTC GATTTCTACA CCTTCTACCG CAACTATCTG   960
GGGCATGTGC AGCCAAAAAT CGAACTGAAG CTGAAAGAAC GCGTGGTGCC GATCATGGAA  1020
```

-continued

```
GGGATCCTCA CCGATTCCGG TTATGAAGAG TCTGCGGTCA ACATTCCGAA CCAGGGATTT   1080

ATCAAGCAAC TGCCGGCGTT TATTGCCGTC GAAGTCCCGG CGATTATCGA CCGCAAGGGC   1140

GTGCACGGCA TCAAGGTCGA TATGCCTGCG GGCATCGGTG GCCTGTTGAG CAACCAGATT   1200

GCGATTCACG ATCTGACCGC CGACGCAGTG ATTGAAGGCT CGCGCGACCT GGTTATCCAG   1260

GCGCTGCTGG TGGACTCGGT CAACGATAAA TGCCGCGCGA TACCGGAACT GGTGGACGTG   1320

ATGATCTCAC GCCAGGGGCC GTGGCTCGAT TACCTGAAAT AA                      1362
```

( 2 ) INFORMATION FOR SEQ ID NO:8:

( i ) SEQUENCE CHARACTERISTICS:
    ( A ) LENGTH: 453 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:8:

```
Met Ala Thr Lys Ile Val Leu Val Gly Ala Gly Ser Ala Gln Phe Gly
 1               5                  10                 15

Tyr Gly Thr Leu Gly Asp Ile Phe Gln Ser Lys Thr Leu Tyr Gly Ser
                20                  25                 30

Glu Ile Val Leu His Asp Ile Asn Pro Thr Ser Leu Ala Val Thr Glu
             35                 40                 45

Lys Thr Ala Arg Asp Phe Leu Ala Ala Glu Asp Leu Pro Phe Ile Val
     50                  55                 60

Ser Ala Thr Thr Asp Arg Lys Thr Ala Leu Ser Gly Ala Glu Phe Val
 65                 70                 75                  80

Ile Ile Ser Ile Glu Val Gly Asp Arg Phe Ala Leu Trp Asp Leu Asp
                85                  90                 95

Trp Gln Ile Pro Gln Gln Tyr Gly Ile Gln Gln Val Tyr Gly Glu Asn
               100                 105                110

Gly Gly Pro Gly Gly Leu Phe His Ser Leu Arg Ile Ile Pro Pro Ile
            115                 120                125

Leu Asp Ile Cys Ala Asp Val Ala Asp Ile Cys Pro Asn Ala Trp Val
    130                 135                 140

Phe Asn Tyr Ser Asn Pro Met Ser Arg Ile Cys Thr Thr Val His Arg
145                 150                 155                 160

Arg Phe Pro Gln Leu Asn Phe Val Gly Met Cys His Glu Ile Ala Ser
                165                 170                175

Leu Glu Arg Tyr Leu Pro Glu Met Leu Gly Thr Ser Phe Asp Asn Leu
            180                 185                 190

Thr Leu Arg Ala Ala Gly Leu Asn His Phe Ser Val Leu Leu Glu Ala
         195                200                 205

Ser Tyr Lys Asp Ser Gly Lys Asp Ala Tyr Ala Asp Val Arg Ala Lys
    210                 215                 220

Ala Pro Asp Tyr Phe Ser Arg Leu Pro Gly Tyr Ser Asp Ile Leu Ala
225                 230                 235                 240

Tyr Thr Arg Asn His Gly Lys Leu Val Glu Thr Glu Gly Ser Thr Glu
                245                 250                255

Arg Asp Ala Leu Gly Gly Lys Asp Ser Ala Tyr Pro Trp Ala Asp Arg
            260                 265                270

Thr Leu Phe Lys Glu Ile Leu Glu Lys Phe His His Leu Pro Ile Thr
    275                 280                 285
```

| | | | | | | | | | | | | | | |
|---|---|---|---|---|---|---|---|---|---|---|---|---|---|---|
| Gly | Asp | Ser | His | Phe | Gly | Glu | Tyr | Ile | Arg | Trp | Ala | Ser | Glu | Val | Ser |
| | 290 | | | | 295 | | | | | 300 | | | | |
| Asp | His | Arg | Gly | Ile | Leu | Asp | Phe | Tyr | Thr | Phe | Tyr | Arg | Asn | Tyr | Leu |
| 305 | | | | | 310 | | | | | 315 | | | | | 320 |
| Gly | His | Val | Gln | Pro | Lys | Ile | Glu | Leu | Lys | Leu | Lys | Glu | Arg | Val | Val |
| | | | | 325 | | | | | 330 | | | | | 335 | |
| Pro | Ile | Met | Glu | Gly | Ile | Leu | Thr | Asp | Ser | Gly | Tyr | Glu | Glu | Ser | Ala |
| | | | 340 | | | | | 345 | | | | | 350 | | |
| Val | Asn | Ile | Pro | Asn | Gln | Gly | Phe | Ile | Lys | Gln | Leu | Pro | Ala | Phe | Ile |
| | | 355 | | | | | 360 | | | | | 365 | | | |
| Ala | Val | Glu | Val | Pro | Ala | Ile | Ile | Asp | Arg | Lys | Gly | Val | His | Gly | Ile |
| | 370 | | | | | 375 | | | | | 380 | | | | |
| Lys | Val | Asp | Met | Pro | Ala | Gly | Ile | Gly | Gly | Leu | Leu | Ser | Asn | Gln | Ile |
| 385 | | | | | 390 | | | | | 395 | | | | | 400 |
| Ala | Ile | His | Asp | Leu | Thr | Ala | Asp | Ala | Val | Ile | Glu | Gly | Ser | Arg | Asp |
| | | | | 405 | | | | | 410 | | | | | 415 | |
| Leu | Val | Ile | Gln | Ala | Leu | Leu | Val | Asp | Ser | Val | Asn | Asp | Lys | Cys | Arg |
| | | | 420 | | | | | 425 | | | | | 430 | | |
| Ala | Ile | Pro | Glu | Leu | Val | Asp | Val | Met | Ile | Ser | Arg | Gln | Gly | Pro | Trp |
| | | 435 | | | | | 440 | | | | | 445 | | | |
| Leu | Asp | Tyr | Leu | Lys | | | | | | | | | | | |
| | | 450 | | | | | | | | | | | | | |

( 2 ) INFORMATION FOR SEQ ID NO:9:

( i ) SEQUENCE CHARACTERISTICS:
        ( A ) LENGTH: 1803 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

```
ATGCCCGTC  AAGGATTGAA  AACTGCACTA  GCGATTTTTC  TAACCACATC  ATTATGCATC    60

TCATGCCAGC  AAGCCTTCGG  TACGCAACAA  CCCTTGCTTA  ACGAAAGAG  TATCGAACAG    120

TCGAAAACCA  TACCTAAATG  GTGGAAGGAG  GCTGTTTTTT  ATCAGGTGTA  TCCGCGCTCC    180

TTAAAGACA  CCAACGGAGA  TGGCATCGGG  GATATTAACG  GCATCATAGA  AAAATTAGAC    240

TATCTAAAAG  CCTTGGGGAT  TGATGCCATT  TGGATCAACC  CACATTATGA  TTCTCCGAAC    300

ACGGATAATG  GTTACGATAT  ACGTGATTAT  CGAAAAATCA  TGAAAGAATA  TGGCACGATG    360

GAGGATTTTG  ACCGCCTGAT  TTCTGAAATG  AAAAAACGGA  ATATGCGGTT  GATGATTGAT    420

GTGGTCATCA  ACCACACCAG  CGATCAAAAC  GAATGGTTTG  TTAAAAGTAA  AAGCAGTAAG    480

GATAATCCTT  ATCGCGGCTA  TTATTTCTGG  AAAGATGCTA  AGAAGGGCA  GGCGCCTAAT    540

AATTACCCTT  CATTCTTTGG  TGGCTCGGCG  TGGCAAAAAG  ATGAAAAGAC  CAATCAATAC    600

TACCTGCACT  ATTTTGCTAA  ACAACAGCCT  GACCTAAACT  GGGATAATCC  CAAAGTCCGT    660

CAAGATCTTT  ATGCAATGTT  ACGTTTCTGG  TTAGATAAAG  GCGTGTCTGG  TTTACGTTTT    720

GATACGGTAG  CGACCTACTC  AAAAATTCCG  GATTTCCCAA  ATCTCACCCA  ACAACAGCTG    780

AAGAATTTTG  CAGCGGAGTA  TACCAAGGGC  CCTAATATTC  ATCGTTACGT  CAATGAAATG    840

AATAAAGAGG  TCTTGTCTCA  TTACGACATT  GCGACTGCCG  GTGAAATCTT  TGGCGTACCC    900

TTGGATCAAT  CGATAAAGTT  CTTCGATCGC  CGCCGTGATG  AGCTGAACAT  TGCATTTACC    960

TTTGACTTAA  TCAGACTCGA  TCGAGACTCT  GATCAAAGAT  GGCGTCGAAA  AGATTGGAAA    1020
```

-continued

```
TTGTCGCAAT TCCGGCAGAT CATCGATAAC GTTGACCGTA CTGCAGGAGA ATATGGTTGG   1080
AATGCCTTCT TCTTGGATAA CCACGACAAT CCGCGCGCTG TCTCGCACTT TGGCGATGAT   1140
CGCCCACAAT GGCGTGAGCC ATCGGCTAAA GCGCTTGCAA CCTTGACGCT GACTCAACGA   1200
GCAACACCTT TTATTTATCA AGGTTCAGAA TTGGGCATGA CCAATTACCC GTTTAAAGCT   1260
ATTGATGAAT TCGATGATAT TGAGGTGAAA GGTTTTTGGC ATGACTACGT TGAGACAGGA   1320
AAGGTCAAAG CCGACGAGTT CTTGCAAAAT GTACGCCTGA CGAGCAGGGA TAACAGCCGG   1380
ACGCCGTTCC AATGGGATGG GAGCAAAAAT GCAGGATTCA CGAGCGGAAA ACCTTGGTTC   1440
AAGGTCAACC CAAACTACCA GGAAATCAAT GCAGTAAGTC AAGTCACACA ACCCGACTCA   1500
GTATTTAACT ATTATCGTCA GTTGATCAAG ATAAGGCATG ACATCCCGGC ACTGACCTAT   1560
GGTACATACA CCGATTTGGA TCCTGCAAAT GATTCGGTCT ACGCCTATAC ACGCAGCCTT   1620
GGGGCGGAAA AATATCTTGT TGTTGTTAAC TTCAAGGAGC AAATGATGAG ATATAAATTA   1680
CCGGATAATT TATCCATTGA GAAAGTGATT ATAGACAGCA ACAGCAAAAA CGTGGTGAAA   1740
AAGAATGATT CATTACTCGA GCTAAAACCA TGGCAGTCAG GGGTTTATAA ACTAAATCAA   1800
TAA                                                                1803
```

( 2 ) INFORMATION FOR SEQ ID NO:10:

( i ) SEQUENCE CHARACTERISTICS:
        ( A ) LENGTH: 600 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Met Pro Arg Gln Gly Leu Lys Thr Ala Leu Ala Ile Phe Leu Thr Thr
 1               5                  10                  15

Ser Leu Cys Ile Ser Cys Gln Gln Ala Phe Gly Thr Gln Gln Pro Leu
            20                  25                  30

Leu Asn Glu Lys Ser Ile Glu Gln Ser Lys Thr Ile Pro Lys Trp Trp
        35                  40                  45

Lys Glu Ala Val Phe Tyr Gln Val Tyr Pro Arg Ser Phe Lys Asp Thr
 50                  55                  60

Asn Gly Asp Gly Ile Gly Asp Ile Asn Gly Ile Ile Glu Lys Leu Asp
 65                  70                  75                  80

Tyr Leu Lys Ala Leu Gly Ile Asp Ala Ile Trp Ile Asn Pro His Tyr
                85                  90                  95

Asp Ser Pro Asn Thr Asp Asn Gly Tyr Asp Ile Arg Asp Tyr Arg Lys
            100                 105                 110

Ile Met Lys Glu Tyr Gly Thr Met Glu Asp Phe Asp Arg Leu Ile Ser
        115                 120                 125

Glu Met Lys Lys Arg Asn Met Arg Leu Met Ile Asp Val Val Ile Asn
130                 135                 140

His Thr Ser Asp Gln Asn Glu Trp Phe Val Lys Ser Lys Ser Ser Lys
145                 150                 155                 160

Asp Asn Pro Tyr Arg Gly Tyr Tyr Phe Trp Lys Asp Ala Lys Glu Gly
                165                 170                 175

Gln Ala Pro Asn Asn Tyr Pro Ser Phe Phe Gly Gly Ser Ala Trp Gln
            180                 185                 190

Lys Asp Glu Lys Thr Asn Gln Tyr Tyr Leu His Tyr Phe Ala Lys Gln
        195                 200                 205
```

| Gln | Pro | Asp | Leu | Asn | Trp | Asp | Asn | Pro | Lys | Val | Arg | Gln | Asp | Leu | Tyr |
|---|---|---|---|---|---|---|---|---|---|---|---|---|---|---|---|
| | 210 | | | | | 215 | | | | 220 | | | | | |

| Ala | Met | Leu | Arg | Phe | Trp | Leu | Asp | Lys | Gly | Val | Ser | Gly | Leu | Arg | Phe |
|---|---|---|---|---|---|---|---|---|---|---|---|---|---|---|---|
| 225 | | | | | 230 | | | | 235 | | | | | | 240 |

| Asp | Thr | Val | Ala | Thr | Tyr | Ser | Lys | Ile | Pro | Asp | Phe | Pro | Asn | Leu | Thr |
|---|---|---|---|---|---|---|---|---|---|---|---|---|---|---|---|
| | | | | 245 | | | | | 250 | | | | | 255 | |

| Gln | Gln | Gln | Leu | Lys | Asn | Phe | Ala | Ala | Glu | Tyr | Thr | Lys | Gly | Pro | Asn |
|---|---|---|---|---|---|---|---|---|---|---|---|---|---|---|---|
| | | | 260 | | | | | 265 | | | | | 270 | | |

| Ile | His | Arg | Tyr | Val | Asn | Glu | Met | Asn | Lys | Glu | Val | Leu | Ser | His | Tyr |
|---|---|---|---|---|---|---|---|---|---|---|---|---|---|---|---|
| | | 275 | | | | | 280 | | | | | 285 | | | |

| Asp | Ile | Ala | Thr | Ala | Gly | Glu | Ile | Phe | Gly | Val | Pro | Leu | Asp | Gln | Ser |
|---|---|---|---|---|---|---|---|---|---|---|---|---|---|---|---|
| | 290 | | | | | 295 | | | | | 300 | | | | |

| Ile | Lys | Phe | Phe | Asp | Arg | Arg | Arg | Asp | Glu | Leu | Asn | Ile | Ala | Phe | Thr |
|---|---|---|---|---|---|---|---|---|---|---|---|---|---|---|---|
| 305 | | | | | 310 | | | | | 315 | | | | | 320 |

| Phe | Asp | Leu | Ile | Arg | Leu | Asp | Arg | Asp | Ser | Asp | Gln | Arg | Trp | Arg | Arg |
|---|---|---|---|---|---|---|---|---|---|---|---|---|---|---|---|
| | | | | 325 | | | | | 330 | | | | | 335 | |

| Lys | Asp | Trp | Lys | Leu | Ser | Gln | Phe | Arg | Gln | Ile | Ile | Asp | Asn | Val | Asp |
|---|---|---|---|---|---|---|---|---|---|---|---|---|---|---|---|
| | | | 340 | | | | | 345 | | | | | 350 | | |

| Arg | Thr | Ala | Gly | Glu | Tyr | Gly | Trp | Asn | Ala | Phe | Phe | Leu | Asp | Asn | His |
|---|---|---|---|---|---|---|---|---|---|---|---|---|---|---|---|
| | | 355 | | | | | 360 | | | | | 365 | | | |

| Asp | Asn | Pro | Arg | Ala | Val | Ser | His | Phe | Gly | Asp | Asp | Arg | Pro | Gln | Trp |
|---|---|---|---|---|---|---|---|---|---|---|---|---|---|---|---|
| | 370 | | | | | 375 | | | | | 380 | | | | |

| Arg | Glu | Pro | Ser | Ala | Lys | Ala | Leu | Ala | Thr | Leu | Thr | Leu | Thr | Gln | Arg |
|---|---|---|---|---|---|---|---|---|---|---|---|---|---|---|---|
| 385 | | | | | 390 | | | | | 395 | | | | | 400 |

| Ala | Thr | Pro | Phe | Ile | Tyr | Gln | Gly | Ser | Glu | Leu | Gly | Met | Thr | Asn | Tyr |
|---|---|---|---|---|---|---|---|---|---|---|---|---|---|---|---|
| | | | | 405 | | | | | 410 | | | | | 415 | |

| Pro | Phe | Lys | Ala | Ile | Asp | Glu | Phe | Asp | Asp | Ile | Glu | Val | Lys | Gly | Phe |
|---|---|---|---|---|---|---|---|---|---|---|---|---|---|---|---|
| | | | 420 | | | | | 425 | | | | | 430 | | |

| Trp | His | Asp | Tyr | Val | Glu | Thr | Gly | Lys | Val | Lys | Ala | Asp | Glu | Phe | Leu |
|---|---|---|---|---|---|---|---|---|---|---|---|---|---|---|---|
| | | 435 | | | | | 440 | | | | | 445 | | | |

| Gln | Asn | Val | Arg | Leu | Thr | Ser | Arg | Asp | Asn | Ser | Arg | Thr | Pro | Phe | Gln |
|---|---|---|---|---|---|---|---|---|---|---|---|---|---|---|---|
| | 450 | | | | | 455 | | | | | 460 | | | | |

| Trp | Asp | Gly | Ser | Lys | Asn | Ala | Gly | Phe | Thr | Ser | Gly | Lys | Pro | Trp | Phe |
|---|---|---|---|---|---|---|---|---|---|---|---|---|---|---|---|
| 465 | | | | | 470 | | | | | 475 | | | | | 480 |

| Lys | Val | Asn | Pro | Asn | Tyr | Gln | Glu | Ile | Asn | Ala | Val | Ser | Gln | Val | Thr |
|---|---|---|---|---|---|---|---|---|---|---|---|---|---|---|---|
| | | | | 485 | | | | | 490 | | | | | 495 | |

| Gln | Pro | Asp | Ser | Val | Phe | Asn | Tyr | Tyr | Arg | Gln | Leu | Ile | Lys | Ile | Arg |
|---|---|---|---|---|---|---|---|---|---|---|---|---|---|---|---|
| | | | 500 | | | | | 505 | | | | | 510 | | |

| His | Asp | Ile | Pro | Ala | Leu | Thr | Tyr | Gly | Thr | Tyr | Thr | Asp | Leu | Asp | Pro |
|---|---|---|---|---|---|---|---|---|---|---|---|---|---|---|---|
| | | 515 | | | | | 520 | | | | | 525 | | | |

| Ala | Asn | Asp | Ser | Val | Tyr | Ala | Tyr | Thr | Arg | Ser | Leu | Gly | Ala | Glu | Lys |
|---|---|---|---|---|---|---|---|---|---|---|---|---|---|---|---|
| | 530 | | | | | 535 | | | | | 540 | | | | |

| Tyr | Leu | Val | Val | Val | Asn | Phe | Lys | Glu | Gln | Met | Met | Arg | Tyr | Lys | Leu |
|---|---|---|---|---|---|---|---|---|---|---|---|---|---|---|---|
| 545 | | | | | 550 | | | | | 555 | | | | | 560 |

| Pro | Asp | Asn | Leu | Ser | Ile | Glu | Lys | Val | Ile | Ile | Asp | Ser | Asn | Ser | Lys |
|---|---|---|---|---|---|---|---|---|---|---|---|---|---|---|---|
| | | | | 565 | | | | | 570 | | | | | 575 | |

| Asn | Val | Val | Lys | Lys | Asn | Asp | Ser | Leu | Leu | Glu | Leu | Lys | Pro | Trp | Gln |
|---|---|---|---|---|---|---|---|---|---|---|---|---|---|---|---|
| | | | 580 | | | | | 585 | | | | | 590 | | |

| Ser | Gly | Val | Tyr | Lys | Leu | Asn | Gln |
|---|---|---|---|---|---|---|---|
| | | 595 | | | | | 600 |

( 2 ) INFORMATION FOR SEQ ID NO:11:

( i ) SEQUENCE CHARACTERISTICS:
( A ) LENGTH: 1794 base pairs (B) TYPE: nucleic acid
(C) STRANDEDNESS: single
(D) TOPOLOGY: linear (ii) MOLECULE TYPE: DNA (genomic)

(ix) FEATURE:
(A) NAME/KEY: misc_RNA
(B) LOCATION: 810
(D) OTHER INFORMATION: /note= "D = Unknown"

(ix) FEATURE:
(A) NAME/KEY: misc_RNA
(B) LOCATION: 1471
(D) OTHER INFORMATION: /note= "S = Unknown"

(xi) SEQUENCE DESCRIPTION: SEQ ID NO:11:

```
ATGTCTTTTG TTACGCTACG TACCGGGGTG GCTGTCGCGC TGTCATCTTT GATAATAAGT    60
CTGGCCTGCC CGGCTGTCAG TGCTGCACCA TCCTTGAATC AGGATATTCA CGTTCAAAAG   120
GAAAGTGAAT ATCCTGCATG GTGGAAAGAA GCTGTTTTTT ATCAGATCTA TCCTCGCTCA   180
TTTAAAGACA CCAATGATGA TGGCATTGGC GATATTCGCG GTATTATTGA AAAGCTGGAC   240
TATCTGAAAT CGCTCGGTAT TGACGCTATC TGGATCAATC CCCATTACGA CTCTCCGAAC   300
ACCGATAACG GCTATGACAT CAGTAATTAT CGTCAGATAA TGAAAGAGTA TGGCACAATG   360
GAGGATTTTG ATAGCCTTGT TGCCGAAATG AAAAAACGAA ATATGCGCTT AATGATCGAC   420
GTGGTCATTA ACCATACCAG TGATCAACAC CCGTGGTTTA TTCAGAGTAA AGCGATAAA   480
AACAACCCTT ATCGTGACTA TTATTTCTGG CGTGACGGAA AAGATAATCA GCCACCTAAT   540
AATTACCCCT CATTTTTCGG CGGCTCGGCA TGGCAAAAAG ATGCAAAGTC AGGACAGTAC   600
TATTTACACT ATTTTGCCAG ACAGCAACCT GATCTCAACT GGGATAACCC GAAAGTACGT   660
GAGGATCTTT ACGCAATGCT CCGCTTCTGG CTGGATAAAG GCGTTTCAGG CATGCGATTT   720
GATACGGTGG CAACTTATTC CAAAATCCCG GGATTTCCCA ATCTGACACC TGAACAACAG   780
AAAAATTTTG CTGAACAATA CACCATGGGD CCTAATATTC ATCGATACAT TCAGGAAATG   840
AACCGGAAAG TTCTGTCCCG GTATGATGTG GCCACCGCGG GTGAAATTTT TGGCGTCCCG   900
CTGGATCGTT CGTCGCAGTT TTTTGATCGC CGCCGACATG AGCTGAATAT GGCGTTTATG   960
TTTGACCTCA TTCGTCTCGA TCGCGACAGC AATGAACGCT GGCGTCACAA GTCGTGGTCG  1020
CTCTCTCAGT TCCGCCAGAT CATCAGCAAA ATGGATGTCA CGGTCGGAAA GTATGGCTGG  1080
AACACGTTCT TCTTAGACAA CCATGACAAC CCCCGTGCGG TATCTCACTT CGGGGATGAC  1140
AGGCCGCAAT GGCGGGAGGC GTCGGCTAAG GCACTGGCGA CGATTACCCT CACTCAGCGG  1200
GCGACGCCGT TTATTTATCA GGGTTCAGAG CTGGGAATGA CTAATTATCC CTTCAGGCAA  1260
CTCAACGAAT TGACGACAT CGAGGTCAAA GGTTTCTGGC AGGATTATGT CCAGAGTGGA  1320
AAAGTCACGG CCACAGAGTT TCTCGATAAT GTGCGCCTGA CGAGCCGCGA TAACAGCAGA  1380
ACACCTTTCC AGTGGAATGA CACCCTGAAT GCTGGTTTTA CTCGCGGAAA GCCGTGGTTT  1440
CACATCAACC CAAACTATGT GGAGATCAAC SCCGAACGCG AAGAAACCCG CGAAGATTCA  1500
GTGCTGAATT ACTATAAAAA AATGATTCAG CTACGCCACC ATATCCCTGC TCTGGTATAT  1560
GGCGCCTATC AGGATCTTAA TCCACAGGAC AATACCGTTT ATGCCTATAC CCGAACGCTG  1620
GGTAACGAGC GTTATCTGGT CGTGGTGAAC TTTAAGGAGT ACCCGGTCCG CTATACTCTC  1680
CCGGCTAATG ATGCCATCGA GGAAGTGGTC ATTGATACTC AGCAGCAAGG TGCGCCGCAC  1740
AGCACATCCC TGTCATTGAG CCCCTGGCAG GCAGGTGCGT ATAAGCTGCG GTAA         1794
```

(2) INFORMATION FOR SEQ ID NO:12:

( i ) SEQUENCE CHARACTERISTICS:
   ( A ) LENGTH: 597 amino acids
   ( B ) TYPE: amino acid
   ( C ) STRANDEDNESS: single
   ( D ) TOPOLOGY: linear ( i i ) MOLECULE TYPE: peptide ( i x ) FEATURE:
   ( A ) NAME/KEY: Peptide
   ( B ) LOCATION: 270
   ( D ) OTHER INFORMATION: /note= "X = Unknown"

( i x ) FEATURE:
   ( A ) NAME/KEY: Peptide
   ( B ) LOCATION: 491
   ( D ) OTHER INFORMATION: /note= "X = Unknown"

( x i ) SEQUENCE DESCRIPTION: SEQ ID NO:12:

```
Met Ser Phe Val Thr Leu Arg Thr Gly Val Ala Val Ala Leu Ser Ser
1               5                   10                  15

Leu Ile Ile Ser Leu Ala Cys Pro Ala Val Ser Ala Ala Pro Ser Leu
            20                  25                  30

Asn Gln Asp Ile His Val Gln Lys Glu Ser Glu Tyr Pro Ala Trp Trp
        35                  40                  45

Lys Glu Ala Val Phe Tyr Gln Ile Tyr Pro Arg Ser Phe Lys Asp Thr
    50                  55                  60

Asn Asp Asp Gly Ile Gly Asp Ile Arg Gly Ile Ile Glu Lys Leu Asp
65                  70                  75                  80

Tyr Leu Lys Ser Leu Gly Ile Asp Ala Ile Trp Ile Asn Pro His Tyr
                85                  90                  95

Asp Ser Pro Asn Thr Asp Asn Gly Tyr Asp Ile Ser Asn Tyr Arg Gln
                100                 105                 110

Ile Met Lys Glu Tyr Gly Thr Met Glu Asp Phe Asp Ser Leu Val Ala
        115                 120                 125

Glu Met Lys Lys Arg Asn Met Arg Leu Met Ile Asp Val Val Ile Asn
130                 135                 140

His Thr Ser Asp Gln His Pro Trp Phe Ile Gln Ser Lys Ser Asp Lys
145                 150                 155                 160

Asn Asn Pro Tyr Arg Asp Tyr Tyr Phe Trp Arg Asp Gly Lys Asp Asn
                165                 170                 175

Gln Pro Pro Asn Asn Tyr Pro Ser Phe Phe Gly Gly Ser Ala Trp Gln
            180                 185                 190

Lys Asp Ala Lys Ser Gly Gln Tyr Tyr Leu His Tyr Phe Ala Arg Gln
        195                 200                 205

Gln Pro Asp Leu Asn Trp Asp Asn Pro Lys Val Arg Glu Asp Leu Tyr
210                 215                 220

Ala Met Leu Arg Phe Trp Leu Asp Lys Gly Val Ser Gly Met Arg Phe
225                 230                 235                 240

Asp Thr Val Ala Thr Tyr Ser Lys Ile Pro Gly Phe Pro Asn Leu Thr
                245                 250                 255

Pro Glu Gln Gln Lys Asn Phe Ala Glu Gln Tyr Thr Met Xaa Pro Asn
            260                 265                 270

Ile His Arg Tyr Ile Gln Glu Met Asn Arg Lys Val Leu Ser Arg Tyr
        275                 280                 285

Asp Val Ala Thr Ala Gly Glu Ile Phe Gly Val Pro Leu Asp Arg Ser
290                 295                 300

Ser Gln Phe Phe Asp Arg Arg Arg His Glu Leu Asn Met Ala Phe Met
305                 310                 315                 320
```

-continued

```
Phe  Asp  Leu  Ile  Arg  Leu  Asp  Arg  Asp  Ser  Asn  Glu  Arg  Trp  Arg  His
               325                      330                     335
Lys  Ser  Trp  Ser  Leu  Ser  Gln  Phe  Arg  Gln  Ile  Ile  Ser  Lys  Met  Asp
               340                      345                     350
Val  Thr  Val  Gly  Lys  Tyr  Gly  Trp  Asn  Thr  Phe  Phe  Leu  Asp  Asn  His
               355                      360                     365
Asp  Asn  Pro  Arg  Ala  Val  Ser  His  Phe  Gly  Asp  Arg  Pro  Gln  Trp
     370                           375                380
Arg  Glu  Ala  Ser  Ala  Lys  Ala  Leu  Ala  Thr  Ile  Thr  Leu  Thr  Gln  Arg
385                      390                     395                          400
Ala  Thr  Pro  Phe  Ile  Tyr  Gln  Gly  Ser  Glu  Leu  Gly  Met  Thr  Asn  Tyr
                    405                      410                     415
Pro  Phe  Arg  Gln  Leu  Asn  Glu  Phe  Asp  Asp  Ile  Glu  Val  Lys  Gly  Phe
               420                      425                     430
Trp  Gln  Asp  Tyr  Val  Gln  Ser  Gly  Lys  Val  Thr  Ala  Thr  Glu  Phe  Leu
               435                      440                     445
Asp  Asn  Val  Arg  Leu  Thr  Ser  Arg  Asp  Asn  Ser  Arg  Thr  Pro  Phe  Gln
     450                           455                460
Trp  Asn  Asp  Thr  Leu  Asn  Ala  Gly  Phe  Thr  Arg  Gly  Lys  Pro  Trp  Phe
465                      470                     475                          480
His  Ile  Asn  Pro  Asn  Tyr  Val  Glu  Ile  Asn  Xaa  Glu  Arg  Glu  Glu  Thr
                    485                      490                     495
Arg  Glu  Asp  Ser  Val  Leu  Asn  Tyr  Tyr  Lys  Lys  Met  Ile  Gln  Leu  Arg
               500                      505                     510
His  His  Ile  Pro  Ala  Leu  Val  Tyr  Gly  Ala  Tyr  Gln  Asp  Leu  Asn  Pro
               515                      520                     525
Gln  Asp  Asn  Thr  Val  Tyr  Ala  Tyr  Thr  Arg  Thr  Leu  Gly  Asn  Glu  Arg
     530                           535                540
Tyr  Leu  Val  Val  Val  Asn  Phe  Lys  Glu  Tyr  Pro  Val  Arg  Tyr  Thr  Leu
545                      550                     555                          560
Pro  Ala  Asn  Asp  Ala  Ile  Glu  Glu  Val  Val  Ile  Asp  Thr  Gln  Gln  Gln
                    565                      570                     575
Gly  Ala  Pro  His  Ser  Thr  Ser  Leu  Ser  Leu  Ser  Pro  Trp  Gln  Ala  Gly
               580                      585                     590
Ala  Tyr  Lys  Leu  Arg
               595
```

( 2 ) INFORMATION FOR SEQ ID NO:13:

( i ) SEQUENCE CHARACTERISTICS:
        ( A ) LENGTH: 1782 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: misc_RNA
        ( B ) LOCATION: 1237..1331
        ( D ) OTHER INFORMATION: /note= "N = Unknown"

( x i ) SEQUENCE DESCRIPTION: SEQ ID NO:13:

```
ATGCTTATGA AGAGATTATT CGCCGCGTCT CTGATGCTTG CTTTTTCAAG CGTCTCCTCT      60
GTGAGGGCTG AGGAGGCCGT AAAGCCGGGC GCGCCATGGT GGAAAAGTGC TGTCTTCTAT     120
CAGGTCTATC CGCGCTCGTT CAAGGATACC AACGGTGATG GGATCGGCGA TTTCAAGGA      180
CTGACGGAGA AGCTCGACTA TCTCAAGGGG CTCGGCATAG ACGCCATCTG GATCAATCCA     240
```

-continued

```
CATTACGCGT CTCCCAACAC CGATAATGGC TACGATATCA GCGACTATCG AGAGGTCATG    300
AAGGAATATG GGACGATGGA GGACTTCGAT CGTCTGATGG CTGAGTTGAA GAAGCGCGGC    360
ATGCGGCTCA TGGTTGATGT CGTGATCAAC CATTCGAGTG ACCAACACGA ATGGTTCAAG    420
AGCAGCCGGG CCTCCAAAGA CAATCCCTAC CGTGACTATT ATTTCTGGCG TGACGGCAAA    480
GACGGTCACG AGCCAAACAA TTACCCTTCC TTCTTCGGCG GTTCGGCATG GGAGAAGGAC    540
CCCGTAACCG GGCAATATTA CCTGCATTAT TTCGGTCGTC AGCAGCCAGA TCTGAACTGG    600
GACACGCCGA AGCTTCGCGA GGAACTCTAT GCGATGCTGC GGTTCTGGCT CGACAAGGGC    660
GTATCAGGCA TGCGGTTCGA TACGGTGGCT ACCTACTCGA AGACACCGGG TTTCCCGGAT    720
CTGACACCGG AGCAGATGAA GAACTTCGCG GAGGCCTATA CCCAGGGGCC GAACCTTCAT    780
CGTTACCTGC AGGAAATGCA CGAGAAGGTC TTCGATCATT ATGACGCGGT CACGGCCGGC    840
GAAATCTTCG GCGCTCCGCT CAATCAAGTG CCGCTGTTCA TCGACAGCCG GAGGAAAGAG    900
CTGGATATGG CTTTCACCTT CGATCTGATC CGTTATGATC GCGCACTGGA TCGTTGGCAT    960
ACCATTCCGC GTACCTTAGC GGACTTCCGT CAAACGATCG ATAAGGTCGA CGCCATCGCG   1020
GGCGAATATG GCTGGAACAC GTTCTTCCTC GGCAATCACG ACAATCCCCG TGCGGTATCG   1080
CATTTGGTG ACGATCGGCC GCAATGGCGC GAAGCCTCGG CCAAGGCTCT GGCCACCGTC    1140
ACCTTGACCC AGCGAGGAAC GCCGTTCATC TTCCAAGGAG ATGAACTCGG AATGACCAAC   1200
TACCCCTTCA AGACGCTGCA GGACTTTGAT GATATCNNNN NNNNNNNNNN NNNNNNNNNN   1260
NNNNNNNNNN NNNNNNNNNN NNNNNNNNNN NNNNNNNNNN NNNNNNNNNN NNNNNNNNNN   1320
NNNNNNNNNN NTGTGGCGTT GACTAGCCGA GCAAACGCCC GCACGCCCTT TCAATGGGAT   1380
GACAGTGCTA ATGCGGGATT CACAACTGGC AAGCCTTGGC TAAAGGTCAA TCCAAACTAC   1440
ACTGAGATCA ACGCCGCGCG GGAAATTGGC GATCCTAAAT CGGTCTACAG CTTTTACCGC   1500
AACCTGATCT CAATCCGGCA TGAAACTCCC GCTCTTTCGA CCGGGAGCTA TCGCGACATC   1560
GATCCGAGTA ATGCCGATGT CTATGCCTAT ACGCGCAGCC AGGATGGCGA GACCTATCTG   1620
GTCGTAGTCA ACTTCAAGGC AGAGCCAAGG AGTTTCACGC TTCCGGACGG CATGCATATT   1680
GCCGAAACCC TGATTGAGAG CAGTTCGCCA GCAGCTCCGG CGGCGGGGGC TGCAAGCCTT   1740
GAGCTGCAGC CTTGGCAGTC CGGCATCTAC AAGGTGAAGT AA                      1782
```

( 2 ) INFORMATION FOR SEQ ID NO:14:

( i ) SEQUENCE CHARACTERISTICS:
        ( A ) LENGTH: 593 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Peptide
        ( B ) LOCATION: 413..444
        ( D ) OTHER INFORMATION: /note= "Xaa = Unknown"

( x i ) SEQUENCE DESCRIPTION: SEQ ID NO:14:

```
Met Leu Met Lys Arg Leu Phe Ala Ala Ser Leu Met Leu Ala Phe Ser
 1               5                  10                  15

Ser Val Ser Ser Val Arg Ala Glu Glu Ala Val Lys Pro Gly Ala Pro
             20                  25                  30

Trp Trp Lys Ser Ala Val Phe Tyr Gln Val Tyr Pro Arg Ser Phe Lys
         35                  40                  45
```

| | | | | | | | | | | | | | |
|---|---|---|---|---|---|---|---|---|---|---|---|---|---|
| Asp | Thr | Asn | Gly | Asp | Gly | Ile | Gly | Asp | Phe | Lys | Gly | Leu | Thr | Glu | Lys |
| | | 50 | | | | 55 | | | | 60 | | | |
| Leu | Asp | Tyr | Leu | Lys | Gly | Leu | Gly | Ile | Asp | Ala | Ile | Trp | Ile | Asn | Pro |
| 65 | | | | | 70 | | | | | 75 | | | | | 80 |
| His | Tyr | Ala | Ser | Pro | Asn | Thr | Asp | Asn | Gly | Tyr | Asp | Ile | Ser | Asp | Tyr |
| | | | | 85 | | | | | 90 | | | | | 95 |
| Arg | Glu | Val | Met | Lys | Glu | Tyr | Gly | Thr | Met | Glu | Asp | Phe | Asp | Arg | Leu |
| | | | 100 | | | | | 105 | | | | | 110 |
| Met | Ala | Glu | Leu | Lys | Lys | Arg | Gly | Met | Arg | Leu | Met | Val | Asp | Val | Val |
| | | | 115 | | | | 120 | | | | | 125 |
| Ile | Asn | His | Ser | Ser | Asp | Gln | His | Glu | Trp | Phe | Lys | Ser | Ser | Arg | Ala |
| | 130 | | | | | 135 | | | | | 140 |
| Ser | Lys | Asp | Asn | Pro | Tyr | Arg | Asp | Tyr | Tyr | Phe | Trp | Arg | Asp | Gly | Lys |
| 145 | | | | | 150 | | | | | 155 | | | | | 160 |
| Asp | Gly | His | Glu | Pro | Asn | Asn | Tyr | Pro | Ser | Phe | Phe | Gly | Gly | Ser | Ala |
| | | | | 165 | | | | | 170 | | | | | 175 |
| Trp | Glu | Lys | Asp | Pro | Val | Thr | Gly | Gln | Tyr | Tyr | Leu | His | Tyr | Phe | Gly |
| | | | 180 | | | | | 185 | | | | | 190 |
| Arg | Gln | Gln | Pro | Asp | Leu | Asn | Trp | Asp | Thr | Pro | Lys | Leu | Arg | Glu | Glu |
| | | 195 | | | | | 200 | | | | | 205 |
| Leu | Tyr | Ala | Met | Leu | Arg | Phe | Trp | Leu | Asp | Lys | Gly | Val | Ser | Gly | Met |
| 210 | | | | | 215 | | | | | 220 |
| Arg | Phe | Asp | Thr | Val | Ala | Thr | Tyr | Ser | Lys | Thr | Pro | Gly | Phe | Pro | Asp |
| 225 | | | | | 230 | | | | | 235 | | | | | 240 |
| Leu | Thr | Pro | Glu | Gln | Met | Leu | Asn | Phe | Ala | Glu | Ala | Tyr | Thr | Gln | Gly |
| | | | | 245 | | | | | 250 | | | | | 255 |
| Pro | Asn | Leu | His | Arg | Tyr | Leu | Gln | Glu | Met | His | Glu | Lys | Val | Phe | Asp |
| | | | 260 | | | | | 265 | | | | | 270 |
| His | Tyr | Asp | Ala | Val | Thr | Ala | Gly | Glu | Ile | Phe | Gly | Ala | Pro | Leu | Asn |
| | | | 275 | | | | 280 | | | | | 285 |
| Gln | Val | Pro | Leu | Phe | Ile | Asp | Ser | Arg | Arg | Lys | Glu | Leu | Asp | Met | Ala |
| | 290 | | | | | 295 | | | | | 300 |
| Phe | Thr | Phe | Asp | Leu | Ile | Arg | Tyr | Asp | Arg | Ala | Leu | Asp | Arg | Trp | His |
| 305 | | | | | 310 | | | | | 315 | | | | | 320 |
| Thr | Ile | Pro | Arg | Thr | Leu | Ala | Asp | Phe | Arg | Gln | Thr | Ile | Asp | Lys | Val |
| | | | 325 | | | | | 330 | | | | | 335 |
| Asp | Ala | Ile | Ala | Gly | Glu | Tyr | Gly | Trp | Asn | Thr | Phe | Phe | Leu | Gly | Asn |
| | | | 340 | | | | | 345 | | | | | 350 |
| His | Asp | Asn | Pro | Arg | Ala | Val | Ser | His | Phe | Gly | Asp | Asp | Arg | Pro | Gln |
| | | 355 | | | | | 360 | | | | | 365 |
| Trp | Arg | Glu | Ala | Ser | Ala | Lys | Ala | Leu | Ala | Thr | Val | Thr | Leu | Thr | Gln |
| | 370 | | | | | 375 | | | | | 380 |
| Arg | Gly | Thr | Pro | Phe | Ile | Phe | Gln | Gly | Asp | Glu | Leu | Gly | Met | Thr | Asn |
| 385 | | | | | 390 | | | | | 395 | | | | | 400 |
| Tyr | Pro | Phe | Lys | Thr | Leu | Gln | Asp | Phe | Asp | Asp | Ile | Xaa | Xaa | Xaa | Xaa |
| | | | | 405 | | | | | 410 | | | | | 415 |
| Xaa | Xaa | Xaa | Xaa | Xaa | Xaa | Xaa | Xaa | Xaa | Xaa | Xaa | Xaa | Xaa | Xaa | Xaa | Xaa |
| | | | 420 | | | | | 425 | | | | | 430 |
| Xaa | Xaa | Xaa | Xaa | Xaa | Xaa | Xaa | Xaa | Xaa | Xaa | Xaa | Xaa | Val | Ala | Leu | Thr |
| | | 435 | | | | | 440 | | | | | 445 |
| Ser | Arg | Ala | Asn | Ala | Arg | Thr | Pro | Phe | Gln | Trp | Asp | Asp | Ser | Ala | Asn |
| 450 | | | | | 455 | | | | | 460 |
| Ala | Gly | Phe | Thr | Thr | Gly | Lys | Pro | Trp | Leu | Lys | Val | Asn | Pro | Asn | Tyr |
| 465 | | | | | 470 | | | | | 475 | | | | | 480 |

| | | | | | | | | | | | | | | |
|---|---|---|---|---|---|---|---|---|---|---|---|---|---|---|
|Thr|Glu|Ile|Asn|Ala|Ala|Arg|Glu|Ile|Gly|Asp|Pro|Lys|Ser|Val|Tyr|
| | | | |485| | | |490| | | |495| | |
|Ser|Phe|Tyr|Arg|Asn|Leu|Ile|Ser|Ile|Arg|His|Glu|Thr|Pro|Ala|Leu|
| | | |500| | | |505| | | | |510| | |
|Ser|Thr|Gly|Ser|Tyr|Arg|Asp|Ile|Asp|Pro|Ser|Asn|Ala|Asp|Val|Tyr|
| | |515| | | |520| | | |525| | | | |
|Ala|Tyr|Thr|Arg|Ser|Gln|Asp|Gly|Glu|Thr|Tyr|Leu|Val|Val|Val|Asn|
| |530| | | |535| | | | |540| | | | | |
|Phe|Lys|Ala|Glu|Pro|Arg|Ser|Phe|Thr|Leu|Pro|Asp|Gly|Met|His|Ile|
|545| | | |550| | | | |555| | | | | |560|
|Ala|Glu|Thr|Leu|Ile|Glu|Ser|Ser|Ser|Pro|Ala|Ala|Pro|Ala|Ala|Gly|
| | | |565| | | | |570| | | |575| | | |
|Ala|Ala|Ser|Leu|Glu|Leu|Gln|Pro|Trp|Gln|Ser|Gly|Ile|Tyr|Lys|Val|
| | |580| | | |585| | | |590| | | | | |
|Lys|

(2) INFORMATION FOR SEQ ID NO:15:

(i) SEQUENCE CHARACTERISTICS:
(A) LENGTH: 1704 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:15:

```
ATGACTGAAA AGTTATCCTT CGAGTCGACA ACAATCTCGC GTCGCTGGTG GAAAGAGGCT      60
GTTGTCTATC AGGTGTATCC CCGCTCGTTC CAGGATTCGA ACGGGACGG CATCGGCGAC      120
CTTCCGGGCA TAACTGCGAG GCTAGATTAC ATCCTCGGTC TAGGCGTTAG TGTCATCTGG     180
CTCAGCCCCC ATTTCGACTC TCCGAATGCT GACAACGGCT ACGATATCCG TGACTATCGC     240
AAGGTGATGC GCGAATTCGG CACCATGGCG GATTTCGATC ACCTGCTGGC CGAGACGAAA     300
AAGCGCGGCA TGCGGCTGAT CATCGATCTC GTCGTCAACC ATACCAGCGA CGAGCATGTC     360
TGGTTTGCCG AAAGCCGGGC CTCGAAAAAC AGCCCGTACC GTGATTACTA CATCTGGCAT     420
CCCGGCCGGG ACGGCGCCGA GCCGAACGAC TGGCGCTCAT TTTTCTCGGG CTCGGCATGG     480
ACTTTCGACC AGCCAACCGG CGAATACTAC ATGCATCTTT CGCCGATAA ACAGCCGGAT     540
ATCAACTGGG ACAATCCGGC TGTGCGCGCC GATGTCTATG ACATCATGCG CTTTTGGCTG     600
GACAAGGGCG TCGACGGATT CCGCATGGAT GTCATCCCCT TCATCTCCAA GCAAGACGGC     660
CTGCCCGACT ATCCTGACCA TCATCGCGGC GCGCCGCAGT TTTTCCACGG TTCGGGTCCC     720
CGCTTGCACG ACTATCTTCA GGAAATGAAC CGCGAGGTAT TGTCGCATTA CGATGTGATG     780
ACGGTTGGCG AGGCCTTCGG TGTGACGGCG GATGCGACGC CGCTTCTGGT CGACGAACGG     840
CGCCGCGAAC TGAACATGAT CTTCAATTTC GACGCCGTGC GCATCGGCCG TGGCGAGACC     900
TGGCACACTA GCCTTGGGC CCTGCCGGAA CTTAAGGCGA TCTATGCCCG TCTGGACGCT     960
GCGACCGACC AGCACTGCTG GGTACGGTC TTTCTCTCCA ACCACGACAA TCCTCGTCTC    1020
GTCTCCCGGT TCGGTGATGA TCATCCTGAC TGGCGGGTGG CGTCGGCCAA GGTTCTTGCC    1080
ACACTTCTCC TAACGCTGAA GGGCACGCCT TCATCTACC AAGGCGATGA ATTGGGCATG    1140
ACCAACTATC CTCGGCTCGG TCGAGGAGAC GACGATATCG AGGTGCGCAA CGCCTGGCAG    1200
GCTGAGGTCA TGACCGGTAA GGCGGATGCA GCCGAATTTC TCGGGGAGAT GCTGAAGATT    1260
TCCCGCGATC ATTCCCGCAC ACCGATGCAA TGGGACGCCA GTCTCGACGG TGGTTTCACT    1320
```

-continued

```
CGGGGTGAAA AGCCCTGGCT ATCGGTCAAT CCGAACTATC GGGCGATCAA TGCGGATGCG   1380
GCACTCGCCG ATCCCGATTC GATCTACCAT TATTACGCCG CACTCATCCG TTTCCGGCGC   1440
GAGACACCGG CGCTCATCTA CGGCGATTAT GACGACTTGG CGCCGGATCA TCCGCACCTC   1500
TTCGTCTATA CAAGAACATT GGGGTCCGAG CGCTATCTGG TCGCGCTTAA CTTCTCCGGC   1560
GATGCGCAGG CACTTGTTCT CCCGACAGAC CTGAGCGCCG CGTCACCTGT TATCGGGCGC   1620
GCCCCGCAAG TGGACCGCAT GCAGCATGAT GCTGCACGGA TCGAGCTGAT GGGTTGGGAA   1680
GCGCGGGTCT ACCACTGCGC ATGA                                         1704
```

(2) INFORMATION FOR SEQ ID NO:16:

(i) SEQUENCE CHARACTERISTICS:
        (A) LENGTH: 567 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

```
Met Thr Glu Lys Leu Ser Phe Glu Ser Thr Thr Ile Ser Arg Arg Trp
 1               5                  10                  15

Trp Lys Glu Ala Val Val Tyr Gln Val Tyr Pro Arg Ser Phe Gln Asp
            20                  25                  30

Ser Asn Gly Asp Gly Ile Gly Asp Leu Pro Gly Ile Thr Ala Arg Leu
        35                  40                  45

Asp Tyr Ile Leu Gly Leu Gly Val Ser Val Ile Trp Leu Ser Pro His
    50                  55                  60

Phe Asp Ser Pro Asn Ala Asp Asn Gly Tyr Asp Ile Arg Asp Tyr Arg
65                  70                  75                  80

Lys Val Met Arg Glu Phe Gly Thr Met Ala Asp Phe Asp His Leu Leu
                85                  90                  95

Ala Glu Thr Lys Lys Arg Gly Met Arg Leu Ile Ile Asp Leu Val Val
            100                 105                 110

Asn His Thr Ser Asp Glu His Val Trp Phe Ala Glu Ser Arg Ala Ser
        115                 120                 125

Lys Asn Ser Pro Tyr Arg Asp Tyr Tyr Ile Trp His Pro Gly Arg Asp
    130                 135                 140

Gly Ala Glu Pro Asn Asp Trp Arg Ser Phe Phe Ser Gly Ser Ala Trp
145                 150                 155                 160

Thr Phe Asp Gln Pro Thr Gly Glu Tyr Tyr Met His Leu Phe Ala Asp
                165                 170                 175

Lys Gln Pro Asp Ile Asn Trp Asp Asn Pro Ala Val Arg Ala Asp Val
            180                 185                 190

Tyr Asp Ile Met Arg Phe Trp Leu Asp Lys Gly Val Asp Gly Phe Arg
        195                 200                 205

Met Asp Val Ile Pro Phe Ile Ser Lys Gln Asp Gly Leu Pro Asp Tyr
    210                 215                 220

Pro Asp His His Arg Gly Ala Pro Gln Phe Phe His Gly Ser Gly Pro
225                 230                 235                 240

Arg Leu His Asp Tyr Leu Gln Glu Met Asn Arg Glu Val Leu Ser His
                245                 250                 255

Tyr Asp Val Met Thr Val Gly Glu Ala Phe Gly Val Thr Ala Asp Ala
            260                 265                 270

Thr Pro Leu Leu Val Asp Glu Arg Arg Arg Glu Leu Asn Met Ile Phe
```

|  | 275 | 280 | 285 |
|---|---|---|---|

Asn Phe Asp Ala Val Arg Ile Gly Arg Gly Glu Thr Trp His Thr Lys
290                    295                300

Pro Trp Ala Leu Pro Glu Leu Lys Ala Ile Tyr Ala Arg Leu Asp Ala
305                310                315                320

Ala Thr Asp Gln His Cys Trp Gly Thr Val Phe Leu Ser Asn His Asp
                325                330                335

Asn Pro Arg Leu Val Ser Arg Phe Gly Asp His Pro Asp Trp Arg
                340                345                350

Val Ala Ser Ala Lys Val Leu Ala Thr Leu Leu Leu Thr Leu Lys Gly
                355                360                365

Thr Pro Phe Ile Tyr Gln Gly Asp Glu Leu Gly Met Thr Asn Tyr Pro
    370                375                380

Arg Leu Gly Arg Gly Asp Asp Ile Glu Val Arg Asn Ala Trp Gln
385                390                395                400

Ala Glu Val Met Thr Gly Lys Ala Asp Ala Ala Glu Phe Lys Gly Glu
                405                410                415

Met Leu Lys Ile Ser Arg Asp His Ser Arg Thr Pro Met Gln Trp Asp
                420                425                430

Ala Ser Leu Asp Gly Gly Phe Thr Arg Gly Glu Lys Pro Trp Leu Ser
    435                440                445

Val Asn Pro Asn Tyr Arg Ala Ile Asn Ala Asp Ala Ala Leu Ala Asp
    450                455                460

Pro Asp Ser Ile Tyr His Tyr Tyr Ala Ala Leu Ile Arg Phe Arg Arg
465                470                475                480

Glu Thr Pro Ala Leu Ile Tyr Gly Asp Tyr Asp Asp Leu Ala Pro Asp
                485                490                495

His Pro His Leu Phe Val Tyr Thr Arg Thr Leu Gly Ser Glu Arg Tyr
            500                505                510

Leu Val Ala Leu Asn Phe Ser Gly Asp Ala Gln Ala Leu Val Leu Pro
        515                520                525

Thr Asp Leu Ser Ala Ala Ser Pro Val Ile Gly Arg Ala Pro Gln Val
    530                535                540

Asp Arg Met Gln His Asp Ala Ala Arg Ile Glu Leu Met Gly Trp Glu
545                550                555                560

Ala Arg Val Tyr His Cys Ala
                565

( 2 ) INFORMATION FOR SEQ ID NO:17:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (geonomic)

( x i ) SEQUENCE DESCRIPTION: SEQ ID NO:17:

TGGTGGAARG ARGCTGT  17

( 2 ) INFORMATION FOR SEQ ID NO:18:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:18:

TCCCAGTTCA GRTCCGGCTG                    20

( 2 ) INFORMATION FOR SEQ ID NO:19:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

AAAGATGGCG KCGAAAAGA                     19

( 2 ) INFORMATION FOR SEQ ID NO:20:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

TGGAATGCCT TYTTCTT                       17

( 2 ) INFORMATION FOR SEQ ID NO:21:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:21:

ATCCCGAAGT GGTGGAAGGA GGC                23

( 2 ) INFORMATION FOR SEQ ID NO:22:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) SEQUENCE DESCRIPTION: SEQ ID NO:22:

CGGAATTCTT ATGCCCCGTC AAGGA              25

( 2 ) INFORMATION FOR SEQ ID NO:23:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) SEQUENCE DESCRIPTION: SEQ ID NO:23:

TGGTGGAAAG AAGCTGT                       17

(2) INFORMATION FOR SEQ ID NO:24:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (geonomic)

(ix) SEQUENCE DESCRIPTION: SEQ ID NO:24:

TCCCAGTTCA GGTCCGGCTG     20

(2) INFORMATION FOR SEQ ID NO:25:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (geonomic)

(xi) SEQUENCE DESCRIPTION: SEQ ID NO:25:

CARTTYGGYT AYGG     14

(2) INFORMATION FOR SEQ ID NO:26:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (geonomic)

(xi) SEQUENCE DESCRIPTION: SEQ ID NO:26:

GTTTCCCAG TCACGAC     17